United States Patent
Lin et al.

(10) Patent No.: US 12,139,679 B2
(45) Date of Patent: Nov. 12, 2024

(54) LUBRICITY MODIFIER FOR FUELS AND APPLICATION THEREOF

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Jianmin Lin, Beijing (CN); Xin Xia, Beijing (CN); Baoshi Li, Beijing (CN); Yan Li, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 17/995,222

(22) PCT Filed: Mar. 30, 2021

(86) PCT No.: PCT/CN2021/083943
§ 371 (c)(1),
(2) Date: Sep. 30, 2022

(87) PCT Pub. No.: WO2021/197323
PCT Pub. Date: Oct. 7, 2021

(65) Prior Publication Data
US 2023/0151290 A1    May 18, 2023

(30) Foreign Application Priority Data

Mar. 30, 2020 (CN) .................... 202010237464.X
Mar. 30, 2020 (CN) .................... 202010240138.4

(51) Int. Cl.
*C10L 10/08* (2006.01)
*C07C 69/60* (2006.01)
*C10L 1/19* (2006.01)

(52) U.S. Cl.
CPC .............. *C10L 10/08* (2013.01); *C07C 69/60* (2013.01); *C10L 1/1905* (2013.01);
(Continued)

(58) Field of Classification Search
CPC ......... C10L 10/08; C10L 1/1905; C07C 69/60
See application file for complete search history.

(56) References Cited

U.S. PATENT DOCUMENTS

| 3,085,002 A | 4/1963 | Lauer |
| 4,402,839 A | 9/1983 | Davis et al. |

(Continued)

FOREIGN PATENT DOCUMENTS

| CN | 1149312 A | 5/1997 |
| CN | 1349556 A | 5/2002 |

(Continued)

OTHER PUBLICATIONS

Richard Jean-Victor et al.; "A comparative study of the thermal properties of homologous series of crystallisable n-alkyl maleate and itaconate monoesters"; Thermochimica Acta, vol. 623, Oct. 30, 2015; ISSN.: 0040-6031; pp. 136-143.
(Continued)

*Primary Examiner* — Ellen M McAvoy
(74) *Attorney, Agent, or Firm* — NKL Law; Allen Xue

(57) ABSTRACT

A lubricity modifier for fuels contain a dicarboxylic acid monoester compound represented by formula (I). In formula (I), $R_1$ represents a single bond, a substituted or unsubstituted $C_{2-6}$ divalent alkenyl group, or a group having a structure of —$R_3$—$R_4$—$R_5$—; $R_2$ represents a substituted or
(Continued)

unsubstituted $C_{1-40}$ hydrocarbyl group; $R_3$ and $R_5$ each independently represents a single bond, or a substituted or unsubstituted $C_{1-3}$ divalent alkyl group; and $R_4$ represents a substituted or unsubstituted $C_{3-12}$ divalent alicyclic group.

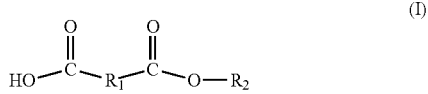

(I)

14 Claims, 1 Drawing Sheet

(52) U.S. Cl.
CPC ...... *C07C 2601/14* (2017.05); *C07C 2601/16* (2017.05); *C10L 2200/0423* (2013.01); *C10L 2200/0446* (2013.01); *C10L 2270/023* (2013.01); *C10L 2270/026* (2013.01)

(56) References Cited

U.S. PATENT DOCUMENTS

| | | | | |
|---|---|---|---|---|
| 5,726,130 | A | * | 3/1998 | Yamanaka ........... C10M 131/14 508/153 |
| 5,882,364 | A | * | 3/1999 | Dilworth ................... C10L 1/18 44/389 |
| 2009/0307964 | A1 | * | 12/2009 | Maehling ................ C10L 10/00 44/329 |
| 2020/0095513 | A1 | * | 3/2020 | Petts ....................... C10L 10/06 |

FOREIGN PATENT DOCUMENTS

| | | | |
|---|---|---|---|
| CN | 1399653 | A | 2/2003 |
| CN | 106929112 | A | 7/2017 |
| CN | 107075405 | A | 8/2017 |
| JP | H0299597 | A | 4/1990 |
| JP | H0953084 | A | 2/1997 |
| RU | 2163251 | C2 | 2/2001 |
| RU | 2600329 | C1 | 10/2016 |

OTHER PUBLICATIONS

Sacha Perocheau Arnaud et al.; "Selective Synthesis of Monoesters of Itaconic Acid with Broad Substrate Scope: Biobased Alternatives to Acrylic Acid?"; ACS Sustainable Chemistry & Engineering, vol. 8, No. 3; Jan. 27, 2020; ISSN.: 2168-0485; pp. 1583-1590.
Pöllmann, Klaus. "Communication pursuant to Article 94(3) EPC"; European Patent Office; Aug. 13, 2024; pp. 1-4.
Grishin D. F. et al.; "Environmentally Friendly Diesel Fuels with Low and Ultralow Sulfur Content and Additives to Them"; Russian Journal of Applied Chemistry; Oct. 25, 2015, vol. 88 pp. 1106-1121.
Arkoudeas P. et al.; "Lubricity Assessment of Gasoline Fuels"; Fuel Processing Technology; Feb. 14, 2014, vol. 122, pp. 107-119.

* cited by examiner

LUBRICITY MODIFIER FOR FUELS AND APPLICATION THEREOF

CROSS REFERENCE TO RELATED APPLICATIONS

This application is a U.S. national stage entry of PCT international application no. PCT/CN2021/083943, filed on Mar. 30, 2021, which claims the priority of Chinese patent application No. 202010237464.X, titled "lubricity additive composition for diesel fuel, its preparation and diesel fuel composition", filed on Mar. 30, 2020; and the priority of Chinese patent application No. 202010240138.4, titled "lubricity additive composition for diesel fuel, its preparation and diesel fuel composition", filed on Mar. 30, 2020, the contents of which are incorporated herein by reference in their entireties.

TECHNICAL FIELD

The present application relates to the field of fuel additives, particularly to an ester-based lubricity modifier for fuels, its preparation and application thereof.

BACKGROUND ART

Because low sulfur diesel fuels have poor lubricity, low sulfur diesel fuels and ultra-low sulfur diesel fuels are often modified with lubricity modifiers (also known as lubricity additives or antiwear additives) to improve their lubricity. This has the advantages of low cost, flexible production, less pollution and the like, and is widely regarded in industry. Existing industrial lubricity additives for low-sulfur diesel fuels are mainly classified as acid-based lubricity additives and ester-based lubricity additives, wherein the acid-based lubricity additives mainly comprise long-chain unsaturated fatty acid such as oleic acid, linoleic acid, linolenic acid and the like, and a typical product is refined tall oil fatty acid. The ester-based lubricity additive is an esterification reaction product of the above fatty acid and a polyhydric alcohol. The use of fatty acid-based lubricity additive for solving the lubricity problem of diesel fuel is relatively low in cost, but due to the upgrading of the diesel fuel emission standard and the deterioration of the lubricity of diesel fuel, it may cause excessive acidity of diesel fuel, an increase of corrosive risk and the like because of the large dosage adopted. Although the dosage of the fatty acid ester-based lubricity additive is small, its cost is high, and the modified diesel fuel may suffer from the problem of emulsification and clouding when meeting water.

The fuel injection system of the aviation turbine engine provides lubrication for all parts by fuel, when the fuel lubricity is deteriorated, the spherical surface of a fuel plunger pump will be seriously abraded, the fuel injection pressure will be reduced, the rotating speed of the engine will decrease, and even an air parking accident may be caused. Therefore, aviation fuels also typically require the addition of lubricity additives to improve their lubricity. Dimer acid obtained by polymerization through Diels-Alder addition reaction using conjugated or non-conjugated unsaturated fatty acid mainly comprising oleic acid, linoleic acid and linolenic acid as raw materials is a main component of aviation fuel lubricity modifiers used in most countries at present. However, dimer acid lubricity additives are expensive to synthesize, and dimer acid itself is expensive as an aviation fuel lubricity modifier.

Gasoline is the lightest, and least lubricious, liquid fuel as compared to other fuels. The lubricating effect of the main component of the gasoline is very prominent because the content of natural antiwear impurities in the gasoline is very low. Moreover, reformulated gasoline also contains significant amounts of oxygen-containing compounds (e.g., lower alcohols, etc.) easily to absorb water and olefins susceptible to oxidization, which may adversely affect the lubricity of gasoline. The improvement of the lubricity of gasoline not only leads to the alleviation of wear of the injection pump and the extension of the life of the engine, but also brings the benefits of an increase in the efficiency of energy utilization and a reduction in the specific fuel consumption. Similar to the solution of the lubricity problem of aviation fuel and diesel fuel, an effective method for improving the lubricity of gasoline is to add a lubricity additive into the gasoline. Existing gasoline lubricity additives mostly use aliphatic amine or ether amine as raw materials, and are expensive in preparation, in addition, the lubricity additive prepared is a nitrogen-containing compound, and thus nitrogen oxides will be generated during the combustion and use of gasoline, which will cause emission pollution, and is contrary to the use principle of clean fuel.

Therefore, there remains a strong need in the art for a lubricity modifier for fuels that can significantly improve the lubricity of fuels and is cost effective for use.

DISCLOSURE OF THE INVENTION

It is an object of the present application to provide a novel lubricity modifier for fuels which can significantly improve the lubricity of fuels and can be used in a relatively low amount, thereby significantly reducing the cost for use of the lubricity modifier.

To achieve the above object, in an aspect, the present application provides a lubricity modifier for fuels comprising a dicarboxylic acid monoester compound represented by the formula (I):

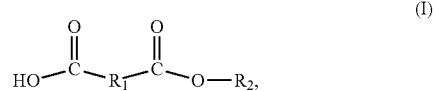

wherein $R_1$ represents a single bond, a substituted or unsubstituted $C_{2-6}$ divalent alkenyl group, or a group having a structure of $—R_3—R_4—R_5—$;

$R_2$ represents a substituted or unsubstituted $C_{1-40}$ hydrocarbyl group;

$R_3$ and $R_5$ each independently represents a single bond, or a substituted or unsubstituted $C_{1-3}$ divalent alkyl group;

$R_4$ represents a substituted or unsubstituted $C_{3-12}$ divalent alicyclic group, wherein the term "substituted" means substituted with at least one $C_{1-4}$ linear or branched hydrocarbyl group.

In another aspect, the present application provides a fuel composition comprising a fuel component and a lubricity modifier according to the present application, wherein the dicarboxylic acid monoester compound is present at an amount of 5 to 400 ppm relative to the mass of the fuel as 100%.

In another aspect, the present application provides a method for improving the lubricity of a fuel, comprising the step of adding a lubricity modifier according to the present application to the fuel, wherein the dicarboxylic acid monoester compound is used in an amount of 5 to 400 ppm relative to the mass of the fuel as 100%.

In a further aspect, the present application provides the use of a dicarboxylic acid monoester compound as a lubricity modifier for fuels, wherein the dicarboxylic acid monoester compound has the following formula (I):

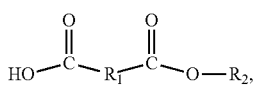

wherein $R_1$ and $R_2$ are as defined above.

In yet another aspect, the present application provides a dicarboxylic acid monoester compound of formula (I) suitable for use as a lubricity modifier for fuels:

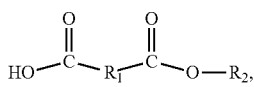

wherein $R_1$ represents a single bond, a substituted or unsubstituted $C_{2-6}$ divalent alkenyl group, or a group having a structure of $—R_3—R_4—R_5—$;

$R_2$ represents a substituted or unsubstituted $C_{5-14}$ linear or branched alkyl;

$R_3$ and $R_5$ each independently represents a single bond, or a substituted or unsubstituted $C_{1-3}$ divalent alkyl group;

$R_4$ represents a substituted or unsubstituted $C_{3-6}$ divalent alicyclic group, wherein the term "substituted" means substituted with at least one $C_{1-4}$ linear or branched hydrocarbyl group.

The lubricity modifier for fuels of the present application has the advantages of easy availability of raw materials, simple and convenient production, capability of remarkably improving the lubricity of fuels, low required addition amount and capability of remarkably reducing the cost for use of the lubricity modifier.

Further, when the lubricity modifier for fuels according to the present application comprises an unsaturated dicarboxylic acid monoester compound having the formula (I), there is no risk of causing emulsification turbidity of diesel fuel, and the anti-emulsification effect is comparable to that of fatty acid-based lubricity modifiers, and superior to that of fatty acid glyceride-based lubricity modifier.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings.

DETAILED DESCRIPTION OF THE INVENTION

Figure 1:
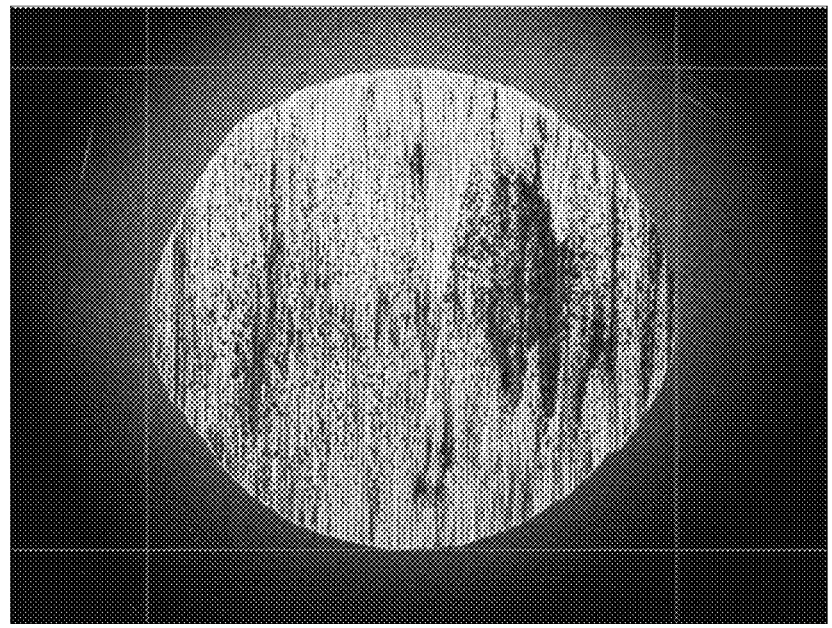
FIG. 1 shows a wear scar photograph of Diesel fuel b as measured on a diesel lubricity tester available from PCS company, UK, with the corrected wear scar diameter (WS1.4) being 651 μm.
Figure 2:
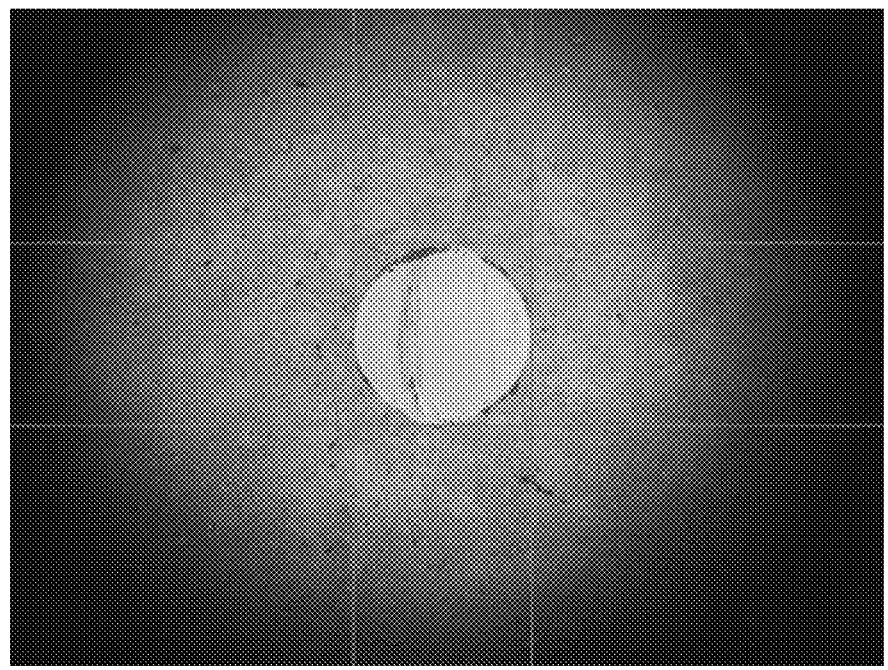
FIG. 2 shows a wear scar photograph of Diesel fuel b measured after adding 200 mg/kg of the monoisooctyl maleate obtained in Example II-1, with the corrected wear scar diameter (WS1.4) being 208 μm.

The present application will be further described hereinafter in detail with reference to specific embodiments thereof and the accompanying drawings. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, for example all values within +5% of said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

In the present application, the term "divalent" group refers to a group obtained by removing 2 hydrogen atoms from the corresponding compound, for example, the term "$C_{2-6}$ divalent alkenyl group" refers to a group obtained by removing two hydrogen atoms from a linear or branched olefin having 2 to 6 carbon atoms, such as ethylene, propylene, 1-butene, 2-butene, isobutylene, pentene, hexene, and the like, in which the carbon-carbon double bond may be located in the main chain or in the side chain of the group; the term "$C_{1-3}$ divalent alkyl group" refers to a group obtained by removing two hydrogen atoms from an alkane having 1 to 3 carbon atoms, such as methylene, ethylene, propylene, and the like; the term "$C_{3-12}$ divalent alicyclic group" refers to a group obtained by removing two hydrogen atoms from a saturated or unsaturated alicyclic hydrocarbon having 3 to 12 carbon atoms, such as cyclopropane, cyclobutane, cyclopentane, cyclopentene, cyclohexane, cyclohexene and the like.

In the present application, the term "hydrocarbyl group" refers to a group obtained by removing one hydrogen atom from an aliphatic hydrocarbon, an alicyclic hydrocarbon or an aromatic hydrocarbon, wherein the term "aliphatic hydrocarbon" refers to a linear or branched, saturated or unsaturated hydrocarbon. For example, as examples of $C_{1-40}$ hydrocarbyl group, there can be mentioned methyl, ethyl, n-propyl, isopropyl, n-butyl, isobutyl, sec-butyl, tert-butyl, n-pentyl, n-hexyl, n-octyl, isooctyl, n-nonyl, isononyl, n-decyl, isodecyl, n-undecyl, isoundecyl, n-dodecyl, n-tridecyl, isotridecyl, 3-hexen-1-yl, octadecenyl, cyclohexyl, p-nonylphenyl, benzyl and the like.

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to the person skilled in the art that such a combination is obviously unreasonable.

All of the patent and non-patent documents cited herein, including but not limited to textbooks and journal articles, are hereby incorporated by reference in their entirety.

As described above, in a first aspect, the present application provides a lubricity modifier for fuels comprising a dicarboxylic acid monoester compound represented by the formula (I):

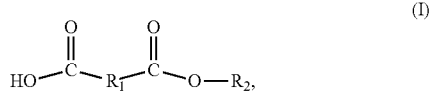

wherein $R_1$ represents a single bond, a substituted or unsubstituted $C_{2-6}$ divalent alkenyl group, or a group having a structure of $-R_3-R_4-R_5-$;
$R_2$ represents a substituted or unsubstituted $C_{1-40}$ hydrocarbyl group;
$R_3$ and $R_5$ each independently represents a single bond, or a substituted or unsubstituted $C_{1-3}$ divalent alkyl group;
$R_4$ represents a substituted or unsubstituted $C_{3-12}$ divalent alicyclic group, wherein the term "substituted" means substituted with at least one $C_{1-4}$ linear or branched hydrocarbyl group.

In a preferred embodiment, $R_1$ represents a single bond, a substituted or unsubstituted $C_{2-4}$ divalent alkenyl group, or a group having a structure of $-R_3-R_4-R_5-$; $R_2$ represents a substituted or unsubstituted $C_{1-18}$ hydrocarbyl group; $R_3$ and $R_5$ each independently represents a single bond or methylene; and $R_4$ represents a substituted or unsubstituted $C_{3-10}$ divalent alicyclic group.

In a preferred embodiment, $R_2$ represents a linear or branched $C_{1-18}$ hydrocarbyl group, $C_{4-18}$ alicyclic hydrocarbyl group, and $C_{7-18}$ aryl-substituted hydrocarbyl group or hydrocarbyl-substituted aryl group.

In some particularly preferred embodiments, the dicarboxylic acid monoester compound is selected from the group consisting of maleic acid monoester, fumaric acid monoester, itaconic acid monoester, citraconic acid monoester, methyl fumaric acid monoester, 2,3-dimethyl maleic acid monoester, glutaconic acid monoester, or any combination thereof; still further preferably, the dicarboxylic acid monoester compound is selected from the group consisting of monomethyl maleate, monoethyl maleate, mono-n-propyl maleate, mono-n-butyl maleate, mono-n-octyl maleate, mono-n-nonyl maleate, mono-n-decyl maleate, mono-n-dodecyl maleate, monomethyl itaconate, monoethyl itaconate, mono-n-propyl itaconate, mono-n-butyl itaconate, mono-n-octyl itaconate, mono-n-decyl itaconate, mono-n-dodecyl itaconate, monoisopropyl maleate, mono-isobutyl maleate, mono-sec-butyl maleate, mono-tert-butyl maleate, mono-isooctyl maleate (mono-2-ethylhexyl maleate), mono-isononyl maleate, mono-isodecyl maleate, isoundecyl maleate, isotridecyl maleate, monoisopropyl itaconate, mono-isobutyl itaconate, mono-isooctyl itaconate, mono-isononyl itaconate, mono-isodecyl itaconate, mono-isoundecyl itaconate, mono-isotridecyl itaconate, mono-3-hexen-1-yl maleate, monooleyl maleate, mono-3-hexen-1-yl itaconate, monooleyl itaconate, monocyclohexyl maleate, monocyclohexyl itaconate, mono-p-nonylphenyl maleate, mono-p-nonylphenyl itaconate, monobenzyl maleate, monobenzyl itaconate, or any combination thereof.

In other particularly preferred embodiments, the dicarboxylic acid monoester compound is selected from the group consisting of 1,2-cyclopentanedicarboxylic acid monoester, 1,2-cyclohexanedicarboxylic acid monoester, tetrahydrophthalic acid monoester, methylhexahydrophthalic acid monoester, methyltetrahydrophthalic acid monoester, 1-methyl-1,2-cyclohexanedicarboxylic acid monoester, 4-methyl-1,2-cyclohexanedicarboxylic acid monoester, 3-methyl-1,2-cyclohexanedicarboxylic acid monoester, 4-methyl-4-cyclohexene-1,2-dicarboxylic acid monoester, 3-methyl-4-cyclohexene-1,2-dicarboxylic acid monoester, or any combination thereof; still further preferably, the dicarboxylic acid monoester compound is selected from the group consisting of 1,2-cyclohexanedicarboxylic acid monoester, tetrahydrophthalic acid monoester, methylhexahydrophthalic acid monoester, methyltetrahydrophthalic acid monoester, or any combination thereof.

The lubricity modifier for fuels of the present application may further comprise an appropriate amount of a fuel and/or organic solvent, a small amount of unreacted raw materials, and inevitable reaction byproducts such as dicarboxylic acid diester compounds.

In a second aspect, the present application provides a method for preparing a lubricity modifier for fuels comprising the step of reacting a dicarboxylic acid of formula (II) or anhydride thereof with an alcohol or phenol of formula (III),

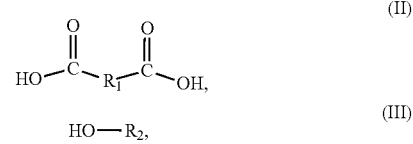

wherein $R_1$ and $R_2$ are as defined above.

In a preferred embodiment, the reaction conditions include: a molar ratio of the dicarboxylic acid or anhydride to the alcohol or phenol of 1:0.5 to 1:1.5, a reaction temperature of 50-250° C., a reaction time of 0.1-10 hr, a reaction pressure of normal pressure or an elevated pressure, the presence or absence of a catalyst, and the presence or absence of a solvent.

In a further preferred embodiment, the reaction conditions include: a molar ratio of the dicarboxylic acid or anhydride to the alcohol or phenol of 1:0.8 to 1:1.3, a reaction temperature of 50-200° C., a reaction time of 1-6 hr, a reaction pressure of normal pressure, and the absence of catalyst and solvent.

In a preferred embodiment, the dicarboxylic acid of formula (II) or anhydride thereof includes, but is not limited to: maleic acid, maleic anhydride, fumaric acid, itaconic acid, itaconic anhydride, citraconic acid, citraconic anhydride, mesaconic acid, 2,3-dimethylmaleic acid, 2,3-dimethylmaleic anhydride, and the like.

In a preferred embodiment, the alcohol or phenol of formula (III) may be an aliphatic alcohol, alicyclic alcohol, aromatic alcohol or phenol having a carbon number of C1-C30, preferably C1-C18. When an aliphatic alcohol is used, its carbon number is C1-C24, preferably C1-C18; when an alicyclic alcohol is used, its carbon number is C3-C20, preferably C4-C10, including but not limited to cyclobutanol, etc.; when an aromatic alcohol or phenol is used, its carbon number is C6-C30, preferably C7-C18.

In the method of the present application, the reaction may be carried out in the presence or absence of a catalyst, and the catalyst may be an acid catalyst, such as one or more selected from the groups consisting of sulfuric acid, hydrochloric acid, p-toluenesulfonic acid, phosphoric acid, boric acid, acidic ion exchange resin, and the like; an ionic liquid catalyst such as 1-butylpyridine/$AlCl_4$ ionic liquid and the like; an inorganic salt solid phase catalyst such as one or more of $FeCl_3$, $AlCl_3$, etc.; a zeolite catalyst such as one or more of ZSM-5, HZSM-5, Al-MCM-41, etc.; a heteropolyacid catalyst such as one or more of PW12/MCM-41, SiW12/MCM-41, etc.; a solid superacid catalyst such as $SO_4^{2-}/ZrO_2$—$TiO_2$, $SO_4^{2-}/TiO_2$—$Al_2O_3$, etc.; and an alkali catalyst such as NaOH, KOH, sodium methoxide, solid superbases, NaH, etc. The reaction may be carried out in the presence or absence of a solvent, and the solvent may be hydrocarbons such as alkanes and aromatic hydrocarbons, for example petroleum ether, gasoline, toluene, xylene, etc.

According to the present application, after the reaction is finished, the product obtained after removal of the catalyst by filtration (if a catalyst is used) can be directly used as the lubricity modifier for fuels of the present application, or alternatively, the product can be separated and purified according to the standard requirements of lubricity additive products, such as by removing the solvent and unreacted raw materials. The solvent and unreacted raw materials meeting the standard requirements do not influence the performance of the lubricity additive of the present application, and where those components are added into a fuel, the performance of the fuel will not be influenced, either.

According to the present application, an appropriate amount of a fuel can be added into the reaction product to obtain a fuel lubricity additive concentrate.

In a third aspect, the present application provides a fuel composition, comprising a fuel component and a lubricity modifier for fuels according to the present application, wherein the dicarboxylic acid monoester compound is present at an amount of 5 to 400 ppm, preferably 10 to 300 ppm, relative to the mass of the fuel component as 100%.

In a preferred embodiment, the fuel component may be selected from diesel fuel, gasoline and aviation fuel.

In some preferred embodiments, the fuel composition is a diesel fuel composition comprising a diesel fuel component and a lubricity modifier for fuels according to the present application, wherein the dicarboxylic acid monoester compound is present at an amount of 10 to 400 ppm, preferably 50 to 300 ppm, relative to the mass of the diesel fuel component as 100%.

According to the present application, the diesel fuel may include various low sulfur diesel fuels. For example, the fuel can be a fuel for compression ignition engine satisfying the Chinese National Standard GB/T 19147 for automobile diesel fuels, which is obtained by blending from a fraction having a distillation range of between 160° C. and 380° C. that is prepared by processing a crude oil (petroleum oil) through various refining processes of an oil refinery, such as atmospheric and vacuum distillation, catalytic cracking, catalytic reforming, coking, hydrofining, hydrocracking and the like.

The diesel fuel may also be a second generation biodiesel oil, derived from renewable resources such as vegetable oils and animal fats, which comprises branched or non-branched long chain hydrocarbons produced through hydrogenation, typically by hydrogenating a plant oil in a refinery, and may be similar in nature and quality to petroleum-based fuels.

The diesel fuel may also be a third generation biodiesel oil, and the third generation biodiesel oil is prepared from non-oil biomass with high cellulose content, such as sawdust, crop straw, solid waste and the like, and microbial oil by gasification and treatment using Fischer-Tropsch technology.

The diesel fuel may also be coal-to-liquid diesel fuel (CTL), which refers to diesel fuel obtained by fischer-tropsch synthesis from coal, or diesel fuel obtained by direct liquefaction of coal. The diesel fuel may also be mixed diesel fuel obtained by adding an oxygen-containing diesel fuel blending component into a petroleum-based diesel fuel, wherein the oxygen-containing diesel fuel blending component refers to an oxygen-containing compound or a mixture of oxygen-containing compounds which can be blended with various diesel fuels to meet certain specification requirements, and is typically alcohols, ethers or a mixture thereof, such as ethanol, polyoxymethylene dimethyl ethers (also referred to as PODEN, DMMn or OME), and the like.

The diesel fuel composition of the present application may further comprise other additives, such as one or more of a phenol-type antioxidant, a polymeric amine-type ashless dispersant, a flow improver, a cetane improver, a metal deactivator, an antistatic agent, a preservative, a rust inhibitor, and a demulsifier, depending on the needs of usage.

The polymeric amine-type ashless dispersant comprises one or more of alkenyl succinimide and/or alkenyl succinic acid amide, Mannich base type ashless dispersant, polyether amine-type ashless dispersant and polyolefin amine-type ashless dispersant. The flow improve is preferably a homopolymer of a (meth)acrylate, and/or a polymer of ethylene and vinyl acetate. The cetane improver can be a nitrate or peroxide, such as isooctyl nitrate, di-t-butyl peroxide, and the like. The metal deactivator may be one or more of ammonium salt formed by benzotriazole and fatty amine, a product obtained by Mannich reaction of benzotriazole, formaldehyde and fatty amine, Schiff base and organic polybasic carboxylic acid.

In some preferred embodiments, the fuel composition is an aviation fuel composition comprising an aviation fuel component and a lubricity modifier for fuels according to the present application, wherein the dicarboxylic acid monoester compound is present at an amount of 5 to 200 ppm, preferably 5 to 50 ppm, relative to the mass of the aviation fuel component as 100%.

According to the present application, the aviation fuel may be a fuel for aviation turbine engines and may be an aviation fuel formulated from a first atmospheric side stream distillate obtained by atmospheric distillation of petroleum refining, a hydrorefining, hydrocracking component produced by a hydroprocessing process, such as aviation fuel No. 3 produced according to GB 6537; or an aviation fuel component produced by coal liquefaction, including direct coal liquefaction and indirect coal liquefaction (Fischer-Tropsch synthesis); or an aviation fuel component produced by Fischer-Tropsch synthesis from syngas; or an aviation fuel produced from renewable biomass feedstocks, such as hydrocarbon aviation fuels produced by hydrodeoxygenation of animal fat and vegetable oil, or waste fats, or an aviation fuel component produced by various catalytic reactions using cellulose or hemicellulose as raw material.

The aviation fuel composition of the present application may also comprise other additives, such as one or more of naphthenic acid or dimer acid-based lubricity additives, metal deactivators, antistatic agents, rust inhibitors, and anti-icing agents, depending on the needs of usage.

In some preferred embodiments, the fuel composition is a gasoline composition comprising a gasoline component and a lubricity modifier for fuels according to the present application, wherein the dicarboxylic acid monoester compound is present at an amount of 5 to 400 ppm, preferably 10 to 300 ppm, relative to the mass of the gasoline component as 100%.

In the context of the present application, the gasoline refers to a refined petroleum fraction having a distillation range of 30 to 220° C. that may comprise suitable additives, which is suitable for use as a fuel in spark-ignition engines, including motor gasoline and aviation piston engine fuel (also known as aviation gasoline). The motor gasoline mainly includes catalytic cracking gasoline, reformed gasoline, aromatic hydrocarbon, alkylated gasoline, isomerized gasoline and the like, and is classified as 4 types, i.e. No. 89, No. 92, No. 95 and No. 98, according to the research octane number. The gasoline described herein may also comprises various oxygen-containing compounds, such as methyl tert-butyl ether (MTBE), ethyl tert-butyl ether (ETBE), tert-amyl methyl ether (TAME), diisopropyl ether (DIPE), methanol, ethanol, butanol, and the like. The gasoline can be motor gasoline, automobile ethanol gasoline and aviation gasoline satisfying the requirements of GB 17930, GB 18351 and GB 1787.

The gasoline composition of the present application may further comprise other additives, such as one or more of an antioxidant, a rust inhibitor, a detergent dispersant, and an anti-knock agent, depending on the needs of usage.

In a fourth aspect, the present application provides a method for improving the lubricity of a fuel, comprising the step of adding a lubricity modifier according to the present application to the fuel, wherein the dicarboxylic acid monoester compound is used in an amount of 5 to 400 ppm, preferably 10 to 300 ppm, relative to the mass of the fuel as 100%.

In some preferred embodiments, the method comprises adding a lubricity modifier according to the present application to a low sulfur diesel fuel, wherein the dicarboxylic acid monoester compound is used in an amount of 10 to 400 ppm, preferably 50 to 300 ppm, relative to the mass of the diesel as 100%.

In some preferred embodiments, the method comprises adding a lubricity modifier according to the present application to an aviation fuel, wherein the dicarboxylic acid monoester compound is used in an amount of 5 to 200 ppm, preferably 5 to 50 ppm, relative to the mass of the aviation fuel as 100%.

In some preferred embodiments, the method comprises adding a lubricity modifier according to the present application to gasoline, wherein the dicarboxylic acid monoester compound is used in an amount of 5 to 400 ppm, preferably 10 to 300 ppm, relative to the mass of the gasoline as 100%.

In a fifth aspect, the present application provides the use of a dicarboxylic acid monoester compound as a lubricity modifier for fuels, wherein the dicarboxylic acid monoester compound has the following formula (I):

$$HO-\underset{\|}{\overset{O}{C}}-R_1-\underset{\|}{\overset{O}{C}}-O-R_2, \quad (I)$$

wherein $R_1$ and $R_2$ are as defined above.

In a sixth aspect, the present application provides a dicarboxylic acid monoester compound of formula (I) suitable for use as lubricity modifier for fuels:

$$HO-\underset{\|}{\overset{O}{C}}-R_1-\underset{\|}{\overset{O}{C}}-O-R_2, \quad (I)$$

wherein $R_1$ represents a single bond, a substituted or unsubstituted $C_{2-6}$ divalent alkenyl group, or a group having a structure of $-R_3-R_4-R_5-$;

$R_2$ represents a substituted or unsubstituted $C_{5-14}$ linear or branched alkyl group;

$R_3$ and $R_5$ each independently represents a single bond, or a substituted or unsubstituted $C_{1-3}$ divalent alkyl group;

$R_4$ represents a substituted or unsubstituted $C_{3-6}$ divalent alicyclic group, wherein the term "substituted" means substituted with at least one $C_{1-4}$ linear or branched hydrocarbyl group.

In a preferred embodiment, the dicarboxylic acid monoester compound is selected from compounds having the following formula:

| No. | Formula (I) | Name of the Compound |
|---|---|---|
| 1 | 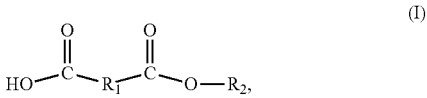 | Monoisononyl maleate (mono-7-methyloctyl maleate) |
| 2 | 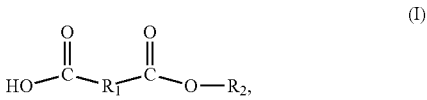 | Monoisoundecyl maleate |

-continued
| No. | Formula (I) | Name of the Compound |
|---|---|---|
| 3 | 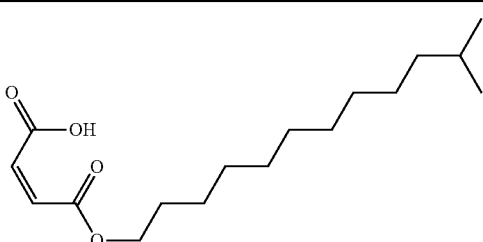 | Monoisotridecyl maleate |
| 4 | 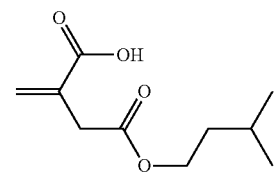 | Isopentyl itaconate |
| 5 | 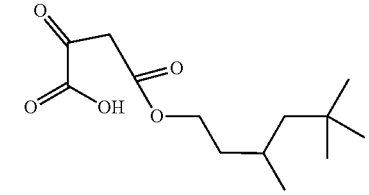 [SMILES: CC(CCOC(=O)CCC(=O)C(=O)O)CC(C)(C)C] | Monoisononyl itaconate (mono-3,5,5-trimethylhexyl itaconate) |
| 6 | 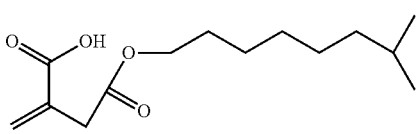 [SMILES: C=C(CC(=O)OCCCCCCC(C)C)C(=O)O] | mono-7-methyloctyl itaconate |
| 7 | 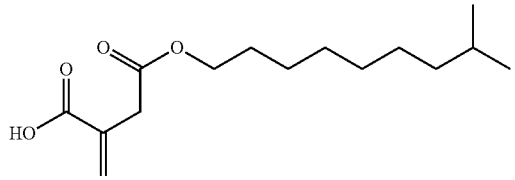 [SMILES: C=C(CC(=O)OCCCCCCCC(C)C)C(=O)O] | Monoisodecyl itaconate |
| 8 | 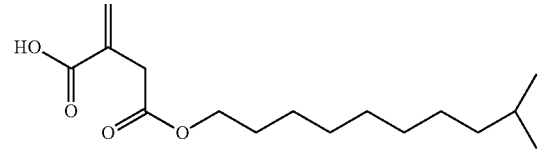 [SMILES: C=C(CC(=O)OCCCCCCCCC(C)C)C(=O)O] | Monoisoundecyl itaconate |
| 9 | 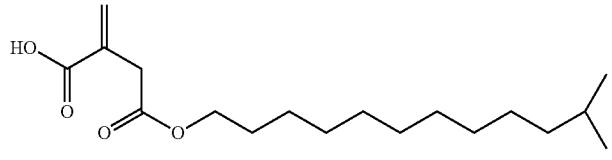 [SMILES: C=C(CC(=O)OCCCCCCCCCCC(C)C)C(=O)O] | Monoisotridecyl itaconate |
| 10 | 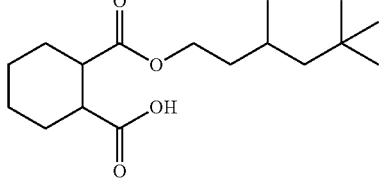 | Monoisononyl cyclohexanedicarboxylate, hexahydrophthalic acid monoisononyl ester |

| No. | Formula (I) | Name of the Compound |
|---|---|---|
| 11 | 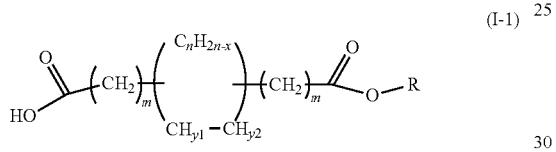 | Monoisononyl methylhexahydrophthalate |

Two particular embodiments of the lubricity modifier for fuels of the present application are described in detail below.

First Class of Embodiments

In a first class of embodiments, the lubricity modifier for fuels of the present application comprises at least a cyclic dicarboxylic acid monoester compound selected from the group consisting of compounds of formula (I-1):

$$\text{HO} \overset{O}{\underset{}{\diagdown}} \text{(CH}_2)_m \overset{C_nH_{2n-x}}{\underset{CH_{y1}-CH_{y2}}{\diagup\diagdown}} \text{(CH}_2)_m \overset{O}{\underset{}{\diagup}} \text{O}-R \quad \text{(I-1)}$$

wherein n is an integer of 1 to 8, m is an integer of 0 to 3, x is an integer of 0 to 8, y1, y2 are integers of 0 to 2, and R represents a $C_{1-30}$ hydrocarbyl group.

In a preferred embodiment, n is an integer of 1 to 6, m is an integer of 0 to 1, x is an integer of 0 to 6, y1, y2 are integers of 0 to 2, and R represents a $C_{1-18}$ hydrocarbyl group.

In a further preferred embodiment, n is 4 or 5, m is 0, x is an integer of 0 to 6, y1, y2 are integers of 0 to 1, and R represents a $C_{4-12}$ hydrocarbyl group.

In a particularly preferred embodiment:
where n is 1, x is 0, y1, y2 are 1, and m is 0, the monoester compound of formula (I-1) is 1,2-cyclopropanedicarboxylic acid monoester;
where n is 1, x is 0, y1, y2 are 1, and m is 1, the monoester compound of formula (I-1) is 1,2-cyclopropanediacetic acid monoester;
where n is 1, x is 2, y1, y2 are 2, and m is 0, the monoester compound of formula (I-1) is 1,1-cyclopropanedicarboxylic acid monoester;
where n is 2, x is 0, y1, y2 are 1, and m is 0, the monoester compound of formula (I-1) is 1,2-cyclobutane dicarboxylic acid monoester;
where n is 2, x is 0, y1, y2 are 1, and m is 1, the monoester compound of formula (I-1) is 1,2-cyclobutanediacetic acid monoester;
where n is 3, x is 0, y1, y2 are 1, and m is 0, the monoester compound of formula (I-1) is 1,2-cyclopentanedicarboxylic acid monoester;
where n is 3, x is 0, y1, y2 are 1, and m is 1, the monoester compound of formula (I-1) is 1,2-cyclopentanediacetic acid monoester;
where n is 3, x is 1, one of y1, y2 is 1 and the other is 2, and m is 0, the monoester compound of formula (I-1) is 1,3-cyclopentanedicarboxylic acid monoester;

where n is 4, x is 0, y1, y2 are 1, and m is 0, the monoester compound of formula (I-1) is 1,2-cyclohexanedicarboxylic acid monoester;
where n is 4, x is 0, y1, y2 are 1, and m is 1, the monoester compound of formula (I-1) is 1,2-cyclohexanediacetic acid monoester;
where n is 4, x is 1, one of y1 and y2 is 1 and the other is 2, and m is 0, the monoester compound of formula (I-1) is 1,3-cyclohexanedicarboxylic acid monoester;
where n is 4, x is 2, y1, y2 are 2, and m is 0, the monoester compound of formula (I-1) is 1,4-cyclohexanedicarboxylic acid monoester;
where n is 4, x is 2, y1, y2 are 1 and m is 0, the monoester compound of formula (I-1) is 4-cyclohexene-1,2-dicarboxylic acid monoester (also called tetrahydrophthalic acid monoester);
where n is 4, x is 2, y1, y2 are 1, and m is 1, the monoester compound of formula (I-1) is 4-cyclohexene-1,2-diacetic acid monoester;
where n is 5, x is 0, y1, y2 are 1, and m is 0, the monoester compound of formula (I-1) is 3-methyl-1,2-cyclohexanedicarboxylic acid monoester (also called 3-methylhexahydrophthalic acid monoester), 4-methyl-1,2-cyclohexanedicarboxylic acid monoester (also called 4-methylhexahydrophthalic acid monoester), or the like;
where n is 5, x is 2, y1, y2 are 1, and m is 0, the monoester compound of formula (I-1) is methyl tetrahydrophthalic monoester, 4-methyl-4-cyclohexene-1,2-dicarboxylic monoester, 3-methyl-4-cyclohexene-1,2-dicarboxylic monoester, or the like.

According to the present application, the cyclic dicarboxylic acid monoester compound is preferably selected from the group consisting of 1,2-cyclopentanedicarboxylic acid monoester, 1,2-cyclohexanedicarboxylic acid monoester, tetrahydrophthalic acid monoester, methylhexahydrophthalic acid monoester, methyltetrahydrophthalic acid monoester, 1-methyl-1,2-cyclohexanedicarboxylic acid monoester, 4-methyl-1,2-cyclohexanedicarboxylic acid monoester, 3-methyl-1,2-cyclohexanedicarboxylic acid monoester, 4-methyl-4-cyclohexene-1,2-dicarboxylic acid monoester, 3-methyl-4-cyclohexene-1,2-dicarboxylic acid monoester; further preferably, the cyclic dicarboxylic acid monoester compound is selected from the group consisting of 1,2-cyclohexanedicarboxylic acid monoester, tetrahydrophthalic acid monoester, methylhexahydrophthalic acid monoester, and methyltetrahydrophthalic acid monoester.

According to the present application, R group in the formula (I-1) may be an aliphatic hydrocarbyl group, an alicyclic hydrocarbyl group or an aromatic hydrocarbyl group. The aliphatic hydrocarbon may be linear or branched, saturated or unsaturated; the unsaturated aliphatic hydrocarbon may be an aliphatic hydrocarbon containing at least one carbon-carbon double bond (ethylenic bond) or at least one carbon-carbon triple bond (acetylenic bond). The alicyclic hydrocarbon may be a saturated alicyclic hydrocarbon (cycloalkane) or an unsaturated alicyclic hydrocarbon. The aromatic hydrocarbon may be monocyclic aromatic hydrocarbon, or may be bicyclic or polycyclic aromatic hydrocarbon. Alicyclic hydrocarbons and aromatic hydrocarbons may have various substituents on their rings.

In a preferred embodiment, R is selected from the group consisting of $C_{1-18}$ aliphatic hydrocarbyl group, $C_{4-18}$ alicyclic hydrocarbyl group, and $C_{7-18}$ aryl-substituted hydrocarbyl group or hydrocarbyl-substituted aryl group.

According to the present application, where R is a saturated aliphatic hydrocarbyl group, R can be a linear alkyl group or a branched alkyl group. Where R is a linear alkyl group, it is preferably a methyl group, an ethyl group, a n-propyl group, a n-butyl group, a n-pentyl group, a n-hexyl group, a n-heptyl group, a n-octyl group, a n-nonyl group, a n-decyl group, a n-undecyl group, a mono-n-dodecyl group (lauryl ester group), a n-tetradecyl group, a n-hexadecyl group, a n-octadecyl group or the like. Where R is a branched alkyl group, it is preferably an isopropyl group, an isobutyl group, a sec-butyl group, an isopentyl group, an isohexyl group, an isoheptyl group, an isooctyl group (particularly a 2-ethylhexyl group), an isononyl group, an isodecyl group, an isoundecyl group, an isotridecyl group, an isopentadecyl group, an isoheptadecyl group or the like.

According to the present application, where R is an unsaturated aliphatic hydrocarbyl group, it is preferably allyl, 2-butenyl, 3-butenyl, isopentenyl, 3-hexenyl, 2-octenyl, 3-nonenyl, 2-decenyl, 7-dodecenyl, 1,5-hexadienyl, 2,4-nonadienyl, 2,4-decadienyl, 9,11-dodecadienyl, 9-octadecenyl, or the like.

According to the present application, where R is an alicyclic hydrocarbyl group, it is preferably a cyclobutyl group, a cyclopentyl group, a cyclohexyl group, a 3-cyclohexenyl group, a 2-cyclohexenyl group, or the like.

R may also be a substituted aryl group, such as phenyl, methylphenyl, p-nonylphenyl, p-dodecylphenyl, and the like. R may also be an aliphatic hydrocarbyl group having an aromatic ring, such as benzyl (phenylmethyl), phenylethyl, etc.

In a particularly preferred embodiment, the cyclic dicarboxylic acid monoester compound is selected from the group consisting of monobutyl 1,2-cyclohexanedicarboxylate, monooctyl 1,2-cyclohexanedicarboxylate, monoisooctyl 1,2-cyclohexanedicarboxylate, monoisononyl 1,2-cyclohexanedicarboxylate, monobutyl tetrahydrophthalate, monooctyl tetrahydrophthalate, monoisooctyl tetrahydrophthalate, monoisononyl tetrahydrophthalate, monobutyl phthalate, monooctyl phthalate, monoisooctyl phthalate, monosec-octyl phthalate, monoisononyl phthalate, monobutyl methylhexahydrophthalate, monooctyl methylhexahydrophthalate, monoisooctyl methylhexahydrophthalate, monoisononyl methylhexahydrophthalate, monolauryl methylhexahydrophthalate, monobutyl methyltetrahydrophthalate, monooctyl methyltetrahydrophthalate, monoisooctyl methyltetrahydrophthalate, monoisononyl methyltetrahydrophthalate, monolauryl methyltetrahydrophthalate, and the like.

In a first class of embodiments, the lubricity modifier for fuels of the present application is prepared by reacting a $C_{5-18}$ cyclic dicarboxylic acid of formula (II) or an anhydride thereof with a $C_{1-30}$ alcohol or phenol of formula (III), to produce a cyclic dicarboxylic acid monoester compound of formula (I-1).

In a preferred embodiment, the conditions of the reaction include: a molar ratio of $C_{5-18}$ cyclic dicarboxylic acid or anhydride thereof to $C_{1-30}$ alcohol or phenol of 1:0.5 to 1:1.5, a reaction temperature of 50-250° C., and a reaction time of 0.1-10 hr.

Second Class of Embodiments

In a second embodiment, the lubricity modifier for fuels of the present application comprises at least an unsaturated dicarboxylic acid monoester compound represented by the formula (I-2):

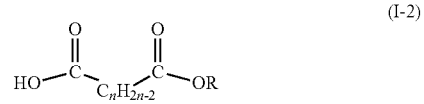

(I-2)

wherein n is an integer of 2 to 6, and R represents a $C_{1-40}$ hydrocarbyl group.

In a preferred embodiment, n is an integer of 2 to 4 and R represents a $C_{1-18}$ hydrocarbyl group.

In the present application, the unsaturated dicarboxylic acid monoester compound refers to a monoester obtained by esterifying either carboxyl group of an $C_{4-8}$ dicarboxylic acid compound having a carbon-carbon unsaturated double bond in the molecule.

In a preferred embodiment, where n is 2, the compound represented by the formula (I-2) is a maleic acid monoester, fumaric acid monoester; where n is 3, the compound represented by the formula (I-2) is itaconic acid monoester, citraconic acid monoester (methyl maleic acid monoester), mesaconic acid monoester (methyl fumaric acid monoester), glutaconic acid monoester, or the like; where n is 4, the compound represented by the formula (I-2) is preferably 2,3-dimethylmaleic acid monoester, ethylmaleic acid monoester, hexenedioic acid monoester, or the like.

In a preferred embodiment, the unsaturated dicarboxylic acid monoester compound is selected from the group consisting of maleic acid monoester, fumaric acid monoester, itaconic acid monoester, citraconic acid monoester (methyl maleic monoester), mesaconic acid monoester (methyl fumaric acid monoester), 2,3-dimethyl maleic acid monoester, glutaconic acid monoester, and the like.

In a particularly preferred embodiment, the unsaturated dicarboxylic acid monoester compound is selected from maleic acid monoesters represented by formula (I-2-1) and itaconic acid monoesters represented by formula (I-2-2) or formula (I-2-3):

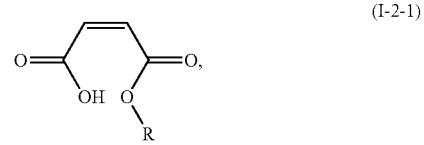

(I-2-1)

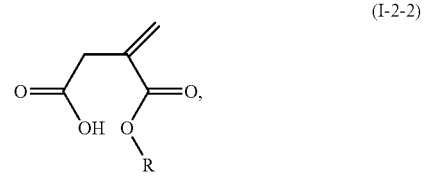

(I-2-2)

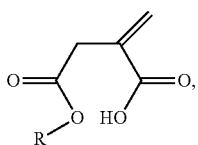

(I-2-3)

wherein R represents a $C_{1-30}$ hydrocarbyl group, preferably a $C_{1-18}$ hydrocarbyl group.

According to the present application, R group in the formulae (I-2), (I-2-1), (I-2-2) and (I-2-3) may be an aliphatic hydrocarbyl group, an alicyclic hydrocarbyl group or an aromatic hydrocarbyl group. The aliphatic hydrocarbon may be linear or branched, saturated or unsaturated; the unsaturated aliphatic hydrocarbon may be an aliphatic hydrocarbon having at least one carbon-carbon double bond (ethylenic bond) or at least one carbon-carbon triple bond (acetylenic bond). The alicyclic hydrocarbon may be a saturated alicyclic hydrocarbon (cycloalkane) or an unsaturated alicyclic hydrocarbon. The aromatic hydrocarbon may be monocyclic aromatic hydrocarbon, or may be bicyclic or polycyclic aromatic hydrocarbon. Alicyclic hydrocarbons and aromatic hydrocarbons may have various substituted hydrocarbyl groups on the ring. Further, R is preferably $C_{1-18}$ aliphatic hydrocarbyl group, $C_{4-18}$ alicyclic hydrocarbyl group and $C_{7-18}$ aryl-substituted hydrocarbyl group or alkyl-substituted hydrocarbyl group.

According to the present application, where R is a saturated aliphatic hydrocarbyl group, it may be a linear alkyl group or a branched alkyl group. Where R is a linear alkyl group, the compound of formula (I-2-1) may be selected from the group consisting of monomethyl maleate, monoethyl maleate, mono-n-propyl maleate, mono-n-butyl maleate, mono-n-pentyl maleate, mono-n-hexyl maleate, mono-n-heptyl maleate, mono-n-octyl maleate, mono-n-nonyl maleate, mono-n-decyl maleate, mono-n-undecyl maleate, mono-n-dodecyl maleate (lauryl ester), mono-n-tetradecyl maleate, mono-n-hexadecyl maleate, mono-n-octadecyl maleate, and the like, preferably selected from the group consisting of monomethyl maleate, monoethyl maleate, mono-n-propyl maleate, mono-n-butyl maleate, mono-n-octyl maleate, mono-n-nonyl maleate, mono-n-decyl maleate, mono-n-dodecyl maleate, and the like; the compounds of formulae (I-2-2) and (I-2-3) may be selected from the group consisting of monomethyl itaconate, monoethyl itaconate, mono-n-propyl itaconate, mono-n-butyl itaconate, mono-n-pentyl itaconate, mono-n-hexyl itaconate, mono-n-heptyl itaconate, mono-n-octyl itaconate, mono-n-nonyl itaconate, mono-n-decyl itaconate, mono-n-undecyl itaconate, mono-n-dodecyl itaconate (lauryl itaconate), mono-n-tetradecyl itaconate, mono-n-hexadecyl itaconate, mono-n-octadecyl itaconate, and the like, preferably selected from the group consisting of monomethyl itaconate, monoethyl itaconate, mono-n-propyl itaconate, mono-n-butyl itaconate, mono-n-octyl itaconate, mono-n-decyl itaconate, mono-n-dodecyl itaconate (lauryl itaconate), and the like.

According to the present application, where R is a branched alkyl group, the compound of formula (I-2-1) may be selected from the group consisting of monoisopropyl maleate, monoisobutyl maleate, mono-sec-butyl maleate, mono-tert-butyl maleate, mono-isoamyl maleate, monoisohexyl maleate, monoisooctyl maleate (mono-2-ethylhexyl maleate), monoisononyl maleate, monoisodecyl maleate, monoisoundecyl maleate, monoisododecyl maleate, monoisotridecyl maleate, monoisotetradecyl maleate, monoisopentadecyl maleate, monoisoheptadecyl maleate, and the like, preferably selected from the group consisting of monoisopropyl maleate, monoisobutyl maleate, mono-sec-butyl maleate, monoisooctyl maleate, monoisononyl maleate, monoisodecyl maleate, monoisoundecyl maleate, monoisotridecyl maleate, and the like; the compounds of formulae (I-2-2) and (I-2-3) may be selected from the group consisting of monoisopropyl itaconate, monoisobutyl itaconate, mono-sec-butyl itaconate, mono-tert-butyl itaconate, monoisoamyl itaconate, monoisohexyl itaconate, monoisooctyl itaconate (mono-2-ethylhexyl itaconate), monoisononyl itaconate, monoisodecyl itaconate, monoisoundecyl itaconate, monoisotridecyl itaconate, and the like, preferably selected from the group consisting of monoisopropyl itaconate, monoisobutyl itaconate, monoisooctyl itaconate (mono-2-ethylhexyl itaconate), monoisononyl itaconate, monoisodecyl itaconate, monoisoundecyl itaconate, and the like.

According to the present application, where R is an unsaturated aliphatic hydrocarbyl group, the compound of formula (I-2-1) may be selected from the group consisting of monoallyl maleate, mono-3-buten-1-yl maleate, monoisopentenyl maleate, mono-3-hexen-1-yl maleate, mono-1-hepten-3-yl maleate, monomethylheptenyl maleate, mono-2-octen-1-yl maleate, mono-3-nonen-1-yl maleate, mono-2-decen-1-yl maleate, mono-7-dodecen-1-yl maleate, mono-1,5-hexadienyl maleate, mono-2,4-decadien-1-yl maleate, mono-9,11-dodecadienyl maleate, monooleyl maleate, and the like, preferably selected from the group consisting of monoallyl maleate, mono-3-buten-1-yl maleate, monoisopentenyl maleate, mono-3-hexen-1-yl maleate, mono-1-hepten-3-yl maleate, monomethylheptenyl maleate, mono-3-nonen-1-yl maleate, mono-2,4-decadien-1-yl maleate, monooleol maleate, and the like; the compounds of formulae (I-2-2) and (I-2-3) may be selected from the group consisting of monoallyl itaconate, mono-2-buten-1-yl itaconate, mono-3-buten-1-yl itaconate, monoisopentenyl itaconate, mono-3-hexen-1-yl itaconate, mono-1-hepten-3-yl itaconate, monomethylheptenyl itaconate, mono-2-octen-1-yl itaconate, mono-3-nonen-1-yl itaconate, mono-2-decen-1-yl itaconate, mono-7-dodecen-1-yl itaconate, mono-1,5-hexadiene itaconate, mono-2,4-nonadien-1-yl itaconate, mono-2,4-decadien-1-yl itaconate, mono-9,11-dodecadienyl itaconate, monooleyl itaconate, and the like, preferably selected from the group consisting of monoallyl itaconate, mono-3-buten-1-yl itaconate, monoisopentenyl itaconate, mono-3-hexen-1-yl itaconate, mono-3-nonen-1-yl itaconate, monooleyl itaconate, and the like.

According to the present application, where R is an alicyclic hydrocarbyl group, the compound of formula (I-2) is preferably selected from the group consisting of monobutyl maleate, monocyclopentyl maleate, monocyclohexyl maleate, mono-3-cyclohexen-1-yl maleate, mono-2-cyclohexenyl maleate, monocyclohexyl itaconate, mono-2-cyclohexenyl itaconate and the like.

According to the present application, where R is a substituted aryl group, the compound of formula (I-2) is preferably selected from the group consisting of mono-p-nonylphenyl maleate, mono-p-dodecylphenyl maleate, mono-p-nonylphenyl itaconate, mono-p-dodecylphenyl itaconate.

According to the present application, where R is an aliphatic hydrocarbyl group having an aromatic ring, the compound of formula (I-2) is preferably selected from the group consisting of monobenzyl maleate, monophenylethyl maleate, monobenzyl itaconate, monophenylethyl itaconate, monophenylpropyl itaconate, and the like.

In a second class of embodiments, the lubricity modifier for fuels of the present application are prepared by reacting a $C_{4-8}$ unsaturated dicarboxylic acid of formula (II) or an anhydride thereof with a $C_{1-30}$ alcohol or phenol of formula (III) to obtain an unsaturated dicarboxylic acid monoester compound of formula (I-2).

In a preferred embodiment, the conditions of the reaction include: a molar ratio of the $C_{4-8}$ unsaturated dicarboxylic acid or an anhydride thereof to the $C_{1-30}$ alcohol or phenol of 1:0.5 to 1:1.5, a reaction temperature of 50-250° C., a reaction time of 0.1-10 hr, and a reaction pressure of normal pressure or an elevated pressure.

In preferred embodiments, the present application provides the following technical solutions:

A1, a diesel lubricity additive composition, comprising at least a cyclic dicarboxylic acid monoester compound selected from compounds of formula (1):

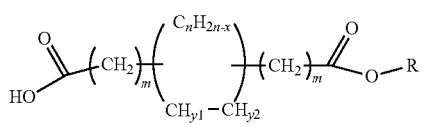

(1)

wherein n is an integer of 1 to 8, m is an integer of 0 to 3, x is an integer of 0 to 8, y1 and y2 are integers of 0 to 2, and R represents a C1-C30 hydrocarbyl group.

A2, the lubricity additive composition according to Item A1, wherein n is an integer of 1 to 6, m is an integer of 0 to 1, x is an integer of 0 to 6, y1 and y2 are integers of 0 to 2, and R represents a C1-C18 hydrocarbyl group.

A3, the lubricity additive composition according to Item A1 or A2, wherein R is selected from the group consisting of C1-C18 linear or branched aliphatic hydrocarbyl groups, C4-C18 cyclic aliphatic hydrocarbyl groups, and C7-C18 aryl-substituted hydrocarbyl groups or hydrocarbyl-substituted aryl groups.

A4, the lubricity additive composition according to Item A1, wherein the cyclic dicarboxylic acid monoester compound is selected from the group consisting of 1,2-cyclopentanedicarboxylic acid monoester, 1,2-cyclohexanedicarboxylic acid monoester, tetrahydrophthalic acid monoester, phthalic acid monoester, methylhexahydrophthalic acid monoester, methyltetrahydrophthalic acid monoester, 1-methyl-1,2-cyclohexanedicarboxylic acid monoester, 4-methyl-1,2-cyclohexanedicarboxylic acid monoester, 3-methyl-1,2-cyclohexanedicarboxylic acid monoester, 4-methyl-4-cyclohexene-1,2-dicarboxylic acid monoester, and 3-methyl-4-cyclohexene-1,2-dicarboxylic acid monoester.

A5, the lubricity additive composition according to Item A1, wherein the cyclic dicarboxylic acid monoester compound is 1,2-cyclohexanedicarboxylic acid monoester, tetrahydrophthalic acid monoester, phthalic acid monoester, methylhexahydrophthalic acid monoester, methyltetrahydrophthalic acid monoester.

A6, a method for preparing a diesel fuel lubricity additive, wherein the lubricity additive is prepared by reacting a C5-C18 cyclic dicarboxylic acid or an anhydride thereof with a C1-C30 alcohol or phenol.

A7, the method according to Item A6, wherein the method comprises: reacting the C5-C18 cyclic dicarboxylic acid or anhydride thereof with the C1-C30 alcohol or phenol at a molar ratio of 1:0.5-1.5, and a reaction temperature of 50-250° C.

A8, the method according to Item A6 or A7, wherein said cyclic dicarboxylic acid or anhydride thereof is selected from the group consisting of 1,2-cyclohexanedicarboxylic acid, phthalic acid, tetrahydrophthalic acid, methyltetrahydrophthalic acid, methylhexahydrophthalic acid, 1,2-cyclohexanedicarboxylic anhydride, hexahydrophthalic anhydride, tetrahydrophthalic anhydride, phthalic anhydride, methyltetrahydrophthalic anhydride, methylhexahydrophthalic anhydride.

A9, the method according to Item A6 or A7, wherein said alcohol or phenol is selected from the group consisting of C1-C18 aliphatic alcohols, C4-C18 alicyclic alcohols, and C7-C18 aromatic alcohols or phenols.

A10, the method according to Item A6 or A7, wherein the alcohol or phenol is selected from the group consisting of methanol, ethanol, propanol, n-butanol, sec-butanol, cyclohexanol, 3-cyclohexene-1-methanol, benzyl alcohol, isooctanol, isononanol, decanol, isodecanol, lauryl alcohol, oleyl alcohol, nonylphenol, and isononanols, isoundecanols, isotridecanols obtained by polymerization of ethylene, propylene or butene.

A11, the method according to Item A6 or A7, wherein the reaction is carried out in the absence of a catalyst or a solvent at a molar ratio of C5-C12 cyclic anhydride to C1-C18 alcohol or phenol of 1:0.8-1.3, a reaction temperature of 60-180° C., and a reaction time of 0.5-10 hr.

A12, the process according to Item A6 or A7, wherein the reaction is carried out in the presence of a catalyst and in the presence or absence of a solvent at a molar ratio of the C5-C12 cyclic dicarboxylic acid to the C1-C18 alcohol or phenol of 1:0.8 to 1.3, a reaction temperature of 70° C. to 250° C., and a reaction time of 3 to 15 hr.

A13, a method for improving the lubricity of diesel fuel, comprising a step of adding the cyclic dicarboxylic acid monoester compound according to any of Items A1 to A5 to a low-sulfur diesel fuel in an amount of 10-400 ppm relative to the mass of the diesel fuel as 100%.

A14, a diesel fuel composition, comprising a low sulfur diesel fuel and the cyclic dicarboxylic acid monoester compound according to any of Items A1 to A5, wherein the cyclic dicarboxylic acid monoester compound is present an amount of 10-400 ppm relative to the mass of the diesel fuel as 100%.

B1, a diesel fuel lubricity additive composition, comprising at least an unsaturated dicarboxylic acid monoester compound of formula (2):

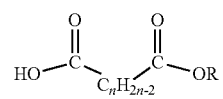

(2)

wherein n is an integer of 2 to 6, wherein R is a C1-C40 hydrocarbyl group.

B2, the lubricity additive composition according to Item B1, wherein n is an integer of 2 to 4, and R represents a C1-C18 hydrocarbyl group.

B3, the lubricity additive composition according to Item B1 or B2, wherein R is selected from C1-C18 linear or branched aliphatic hydrocarbyl groups, C4-C18 cyclic aliphatic hydrocarbyl groups, and C7-C18 aryl-substituted hydrocarbyl groups or hydrocarbyl-substituted aryl groups.

B4, the lubricity additive composition according to Item B1, wherein the unsaturated dicarboxylic acid monoester compound is one or more selected from the group consisting of maleic acid monoester, fumaric acid monoester, itaconic acid monoester, citraconic acid monoester, methyl fumaric acid monoester, 2,3-dimethyl maleic acid monoester, glutaconic acid monoester.

B5, the lubricity additive composition according to Item B1, wherein the unsaturated dicarboxylic acid monoester compound is selected from the group consisting of monomethyl maleate, monoethyl maleate, mono-n-propyl maleate, mono-n-butyl maleate, mono-n-octyl maleate, mono-n-nonyl maleate, mono-n-decyl maleate, mono-n-dodecyl maleate, monomethyl itaconate, monoethyl itaconate, mono-n-propyl itaconate, mono-n-butyl itaconate, mono-n-octyl itaconate, mono-n-decyl itaconate, mono-n-dodecyl itaconate, monoisopropyl maleate, mono-isobutyl maleate, mono-sec-butyl maleate, mono-isooctyl maleate, mono-isodecyl maleate, monoisopropyl itaconate, mono-isobutyl itaconate, mono-isooctyl itaconate, mono-isononyl itaconate, mono-isodecyl itaconate, mono-3-hexene-1-yl maleate, monooleyl maleate, mono-3-hexen-1-yl itaconate, monooleyl itaconate, monocyclohexyl maleate, monocyclohexyl itaconate, mono-p-nonylphenyl maleate, mono-p-nonylphenyl itaconate, monobenzyl maleate, monobenzyl itaconate.

B6, a method for preparing a diesel fuel lubricity additive, wherein the lubricity additive is obtained by reacting a C4-C8 unsaturated dicarboxylic acid or an anhydride thereof with a C1-C30 alcohol or phenol.

B7, the method according to Item B6, comprising: reacting the C4-C8 unsaturated dicarboxylic acid or anhydride thereof with the C1-C30 alcohol or phenol at a molar ratio of 1:0.5-1.5, and a reaction temperature of 50-250° C.

B8, the method according to Item B6 or B7, wherein the unsaturated dicarboxylic acid or anhydride thereof is selected from the group consisting of maleic acid, maleic anhydride, fumaric acid, itaconic anhydride, citraconic acid, citraconic anhydride, methyl fumaric acid, 2,3-dimethyl maleic acid, and 2,3-dimethyl maleic anhydride.

B9, the method according to Item B6 or B7, wherein the alcohol or phenol is selected from the group consisting of C1-C18 aliphatic alcohols, C4-C18 alicyclic alcohols, and C7-C18 aromatic alcohols or phenols.

B10, the method according to Item B6 or B7, wherein the alcohol or phenol is selected from the group consisting of methanol, ethanol, n-propanol, isopropanol, n-butanol, sec-butanol, cyclohexanol, 3-cyclohexene-1-methanol, benzyl alcohol, n-octanol, isooctanol, isononanol, n-decanol, isodecanol, lauryl alcohol, oleyl alcohol, nonyl phenol, and isononanols, isoundecanols, isotridecanols obtained by polymerization of ethylene, propylene or butene.

B11, the method according to Item B6 or B7, comprising: reacting a maleic anhydride or itaconic anhydride with a C1-C18 alcohol or phenol in the absence of a catalyst or a solvent, at a molar ratio of 1:0.8-1.3, a reaction temperature of 50-120° C., and a reaction time of 0.5-8 hr.

B12, the method according to Item B6 or B7, comprising: reacting a maleic acid or itaconic acid with a C1-C18 alcohol or phenol in the presence of a catalyst and in the presence or absence of a solvent at a molar ratio of 1:0.8-1.3, a reaction temperature of 70-250° C., and a reaction time of 3-15 hr.

B13. a method for improving the lubricity of diesel fuel, comprising a step of adding the unsaturated dicarboxylic acid monoester compound according to any of Items B1-B5 to a low-sulfur diesel fuel in an amount of 10-400 ppm, relative to the mass of the diesel as 100%.

B14, a diesel fuel composition, comprising a low-sulfur diesel fuel and the unsaturated dicarboxylic acid monoester compound according to any of Items B1-B5, wherein the unsaturated dicarboxylic acid monoester compound is present at an amount of 10-400 ppm, relative to the mass of the diesel fuel as 100%.

EXAMPLES

The present application will be further illustrated with reference to the following examples, but the present application is not limited thereto.

In the following examples, the lubricity of diesel fuel was evaluated by measuring the Wear Scar Diameter (WSD) at 60° C. on a High-Frequency Reciprocating Rig (HFRR, PCS instruments, UK) according to the SH/T 0765 method, and the influence of temperature and humidity was corrected to obtain the reported result WS 1.4.

The dicarboxylic acid monoester compounds used in the examples and comparative examples of the present application may either be synthesized by the method described herein, or be commercially available industrial products, and are commercially available unless otherwise specified.

The following Test Examples I-1 and I-2 compare the effects of the lubricity modifiers according to the present application (Examples I-1 to I-6) and those of non-inventive lubricity modifiers (Comparative Examples I-1 to I-4) when used in diesel fuel, where the types and sources of the lubricity modifiers used are shown in the following Table I-1:

TABLE I-1

Types and sources of lubricity modifiers used in Test Examples I-1 and I-2

| Example No. | Type of the lubricity modifier | Source |
| --- | --- | --- |
| Example I-1 | Monoisooctyl 1,2-cyclohexanedicarboxylate | Commercially available |
| Example I-2 | Monoisononyl tetrahydrophthalate | Commercially available |
| Example I-3 | Mono-p-nonylphenyl methyl-1,2-cyclohexanedicarboxylate | Commercially available |
| Example I-4 | Monobenzyl methyltetrahydrophthalate | Commercially available |
| Examples I-5 | Monoisononyl cyclohexanedicarboxylate | Self-made |
| Examples I-6 | Monoisononyl methylhexahydrophthalate | Self-made |

TABLE I-1-continued

Types and sources of lubricity modifiers used in Test Examples I-1 and I-2

| Example No. | Type of the lubricity modifier | Source |
|---|---|---|
| Comparative Example I-1 | Diisooctyl hexahydrophthalate (CAS 84-71-9) | Commercial available, purity 97% |
| Comparative Example I-2 | Bis(2-ethylhexyl) phthalate (CAS 117-81-7) | Commercial available, purity 97% |
| Comparative Example I-3 | Fatty acid-based lubricity modifier HiTEC 4140 | Purchased from Afton Inc. |
| Comparative examples I to 4 | Fatty acid ester-based lubricity modifier Infineum R655 | Purchased from Infineum |

The method for preparing the self-made lubricity modifiers listed in Table I-1 is described in detail hereinbelow:

Example I-5

336 g of 1,2-cyclohexane dicarboxylic anhydride (hexahydrophthalic anhydride, available from Nan Ya Plastics Corp (*Formosa* Plastics), Taiwan) and 345.6 g of isononanol (3,5,5-trimethyl-1-hexanol, available from Tokyo Chemical Industry) were charged into a 1000 mL reactor equipped with an electric stirrer, a thermometer and a reflux condenser, the molar ratio of hexahydrophthalic anhydride to isononanol was about 1:1.2, the mixture was heated under stirring to 115° C. and reacted for 3 hours, then the temperature was raised and unreacted isononanol was removed by distillation under reduced pressure to obtain 6202 g of a product mainly comprising monoisononyl 1,2-cyclohexanedicarboxylate.

Example I-6

336 g of methyl-1,2-cyclohexane dicarboxylic anhydride (methylhexahydrophthalic anhydride, with a mass fraction of 99%, available from Guangzhou Kuibang Chemical Co., Ltd.) and 316.8 g of isononanol (3,5,5-trimethyl-1-hexanol, available from Tokyo Chemical Industry) were charged into a 1000 mL reactor equipped with an electric stirrer, a thermometer and a reflux condenser, the molar ratio of methyl-1,2-cyclohexane dicarboxylic anhydride to isononanol was about 1:1.1, and the mixture was heated under stirring to 100° C. and reacted for 4.5 hours to obtain about 770 g of a product mainly comprising monoisononyl methyl-1,2-cyclohexanedicarboxylate.

Test Example I-1

This test example compares the effects of the lubricity modifiers of the examples and comparative examples when used in diesel fuel, in which the lubricity modifiers were blended with petroleum-based Diesel fuel a and Diesel fuel b, respectively, the Diesel fuel a was available from Yanshan Division of Sinopec, and the Diesel fuel b was available from the Gaoqiao Division of Sinopec, and the physico-chemical properties of the Diesel fuel a and the Diesel fuel b are shown in Table I-2. The wear scar diameter WS1.4 of the diesel fuel before and after addition of the lubricity modifiers measured according to HFRR method (ISO 12156-1) is shown in Tables I-3 and I-4, in which a smaller wear scar diameter indicates a better lubricity of the diesel fuel. At present, in most diesel fuel standards in the world, such as European Standard EN 590, China Automotive Diesel fuel Standard GB 19147 and local Automotive Diesel fuel Standard adopted in Beijing DB 11/239, a wear scar diameter of less than 460 μm (60° C.) is used as a criterion for determining whether the lubricity of the diesel fuel is qualified or not.

TABLE I-2

Properties of petroleum-based Diesel fuel a and Diesel fuel b

| Item | Diesel fuel a | Diesel fuel b |
|---|---|---|
| Density (20° C.)/(kg · m$^{-3}$) | 834.1 | 806.2 |
| Initial boiling point/° C. | 192.0 | 210.1 |
| 5% temperature/° C. | 216.8 | 226.3 |
| 10% temperature/° C. | 227.5 | 231.3 |
| 20% temperature/° C. | 240.0 | 236.4 |
| 30% temperature/° C. | 251.2 | 242.1 |
| 40% temperature/° C. | 258.9 | 246.6 |
| 50% temperature/° C. | 269.0 | 250.3 |
| 60% temperature/° C. | 278.8 | 254.3 |
| 70% temperature/° C. | 291.2 | 258.3 |
| 80% temperature/° C. | 305.1 | 263.3 |
| 90% temperature/° C. | 325.6 | 273.6 |
| 95% temperature/° C. | 341.5 | 290.3 |
| Final distillation point/° C. | 345.8 | 305.7 |
| Residual amount (ψ)/% | 1.0 | 1.0 |
| Amount of loss (ψ)/% | 1.4 | 1.3 |
| Acidity/(mgKOH · 100 mL$^{-1}$) | 0.45 | 0.51 |
| Viscosity at 20° C./(mm$^2$ · s$^{-1}$) | 4.512 | 3.421 |
| Viscosity at 40° C./(mm$^2$ · s$^{-1}$) | 2.913 | 2.290 |
| 10% carbon residue, % | <0.05 | <0.05 |
| Ash content, % | <0.002 | <0.002 |
| Cold filter plugging point/° C. | −5 | −29 |
| Freezing Point/° C. | −10 | −36 |
| Closed cup flash point/° C. | 73 | 82 |
| w (sulfury)/mg · L$^{-1}$ | 10 | <5 |
| Water content, % | Trace | Trace |
| Lubricity (HFRR)/μm | 564 | 651 |

TABLE I-3

Wear scar diameter WS1.4 of Diesel fuel a before and after addition of the lubricity modifier as mearsued according to HFRR method

| Oil sample | Dosage of the modifier (mg · kg$^{-1}$) | WS1.4 (μm) |
|---|---|---|
| Diesel fuel a | / | 564 |
| Diesel fuel a + product of Example I-1 (Monoisooctyl 1,2-cyclohexanedicarboxylate) | 150 | 266 |

TABLE I-3-continued

Wear scar diameter WS1.4 of Diesel fuel a before and after addition of the lubricity modifier as mearsued according to HFRR method

| Oil sample | Dosage of the modifier (mg · kg$^{-1}$) | WS1.4 (μm) |
|---|---|---|
| Diesel fuel a + product of Example I-1 (Monoisooctyl 1,2-cyclohexanedicarboxylate) | 80 | 391 |
| Diesel fuel a + isooctanol | 150 | 559 |
| Diesel fuel a + product of Example I-2 (monoisononyl tetrahydrophthalate) | 150 | 257 |
| Diesel fuel a + product of Example I-2 (monoisononyl tetrahydrophthalate) | 80 | 396 |
| Diesel fuel a + isononanol | 150 | 561 |
| Diesel fuel a + product of Example I-3 (mono-p-nonylphenyl methyl-1,2-cy clohexanedicarboxylate) | 150 | 299 |
| Diesel fuel a + p-nonyl phenol | 150 | 559 |
| Diesel fuel a + product of Example I-4 (monobenzyl methy ltetrahy drophthal ate) | 150 | 287 |
| Diesel fuel a + benzyl alcohol | 150 | 551 |
| Diesel fuel a + Comparative Example I-1 (diisooctyl hexahy drophthal ate) | 150 | 538 |
| Diesel fuel a + Comparative Example I-1 (diisooctyl hexahy drophthal ate) | 80 | 547 |
| Diesel fuel a + Comparative Example I-2 (di-(2-ethylhexyl) phthalate) | 150 | 544 |
| Diesel fuel a + Comparative Example I-2 (di-(2-ethylhexyl) phthalate) | 80 | 558 |
| Diesel fuel a + Comparative Example I-3 (HiTEC 4140) | 150 | 427 |
| Diesel fuel a + Comparative Example I-3 (HiTEC 4140) | 80 | 499 |
| Diesel fuel a + Comparative Example I-4 (Infineum R655) | 150 | 394 |
| Diesel fuel a + Comparative Example I-4 (Infineum R655) | 80 | 491 |

TABLE I-4

Wear scar diameter WS1.4 of Diesel fuel b before and after addition of the lubricity modifier as mearsued according to HFRR method

| Oil sample | Dosage of the modifier (mg · kg$^{-1}$) | WS1.4 (μm) |
|---|---|---|
| Diesel fuel b | / | 651 |
| Diesel fuel b + product of Example I-1 (monoisooctyl 1,2-cyclohexanedicarboxylate) | 200 | 296 |
| Diesel fuel b + product of Example I-1 (monoisooctyl 1,2-cyclohexanedicarboxylate) | 100 | 401 |
| Diesel fuel b + isooctanol | 200 | 649 |
| Diesel fuel b + product of Example I-2 (monoisononyl tetrahydrophthalate) | 200 | 281 |
| Diesel fuel b + product of Example I-2 (monoisononyl tetrahydrophthalate) | 120 | 395 |
| Diesel fuel b + isononanol | 200 | 631 |
| Diesel fuel b + product of Example I-3 (mono-p-nonylphenyl methyl-1,2-cyclohexanedicarboxylate) | 200 | 311 |
| Diesel fuel b + p-nonyl phenol | 200 | 619 |
| Diesel fuel b + product of Example I-4 (monobenzyl methyltetrahydrophthalate) | 200 | 307 |
| Diesel fuel b + benzyl alcohol | 200 | 651 |
| Diesel fuel b + product of Example I-5 (monoisononyl cyclohexanedicarboxylate) | 200 | 278 |
| Diesel fuel b + product of Example I-5 (monoisononyl cyclohexanedicarboxylate) | 120 | 402 |
| Diesel fuel b + product of Example I-6 (monoisononyl methylhexahydrophthalate) | 200 | 289 |
| Diesel fuel b + product of Example I-6 (monoisononyl methylhexahydrophthalate) | 120 | 398 |
| Diesel fuel b + Comparative Example I-1 (dioctyl tetrahydrophthalate) | 200 | 638 |
| Diesel fuel b + Comparative Example I-1 (dioctyl tetrahydrophthalate) | 120 | 651 |
| Diesel fuel b + Comparative Example I-2 (di-(2-ethylhexyl) phthalate) | 200 | 640 |

TABLE I-4-continued

Wear scar diameter WS1.4 of Diesel fuel b before and after addition of the lubricity modifier as mearsued according to HFRR method

| Oil sample | Dosage of the modifier (mg · kg$^{-1}$) | WS1.4 (μm) |
|---|---|---|
| Diesel fuel b + Comparative Example I-2 (di-(2-ethylhexyl) phthalate) | 120 | 652 |
| Diesel fuel b + Comparative Example I-3 (HiTEC 4140) | 200 | 432 |
| Diesel fuel b + Comparative Example I-3 (HiTEC 4140) | 120 | 519 |
| Diesel fuel b + Comparative Example I-4 (Infineum R655) | 200 | 387 |
| Diesel fuel b + Comparative Example I-4 (Infineum R655) | 120 | 482 |

As can be seen from Tables I-3 and I-4, the alcohol compounds and the phenol compounds have little antiwear effect and can not improve the lubricity of diesel fuel; in contrast, the lubricity of diesel fuel is surprisingly greatly improved by adding the monoester compound of the present application.

For the low-sulfur diesel fuel shown in Table I-3, the monoester compound of the present application can also greatly improve the lubricity of diesel fuel at a very small amount, for example, the wear scar diameter of Diesel fuel a can be reduced from 564 μm to 266 μm and 257 μm at an addition amount of 150 mg/kg of the monoester of Examples I-1 and I-2, while the diisooctyl hexahydrophthalate compound of Comparative Example I-1 shows no effect of improving the lubricity of the diesel fuel; the di-(2-ethylhexyl) phthalate compound of Comparative Example I-2 shows no effect of improving the lubricity of the diesel fuel; even the fatty acid-based (Comparative Example I-3) and fatty acid ester-based (Comparative Example I-4) lubricity modifiers for diesel fuel commonly used in industry at present can only reduce the wear scar diameter of Diesel fuel a to 427 μm and 394 μm at a dosage of 150 mg/kg. When the dosage is further reduced to 80 mg/kg, the monoester compound of the present application can still enable the lubricity of the Diesel fuel a to meet the requirements of the diesel fuel standard, while the compounds of Comparative Examples I-3 and I-4 have poor antiwear effect at such a dosage and is not sufficient to enable the diesel fuel to meet the requirements of the diesel fuel standard, i.e. a wear scar diameter of no more than 460 μm.

For the ultra-low sulfur diesel fuel shown in Table I-4, the monoester compounds of the present application surprisingly improved the lubricity of the diesel fuel at very low amounts. For example, it is surprisingly that the wear scar diameter of Diesel fuel b was reduced from 651 m to 296 μm and 281 μm, respectively, using the monoesters of Examples I-1 and I-2 at a dosage of 200 mg/kg.

The diisooctyl hexahydrophthalate of Comparative Example I-1, when added at a dosage of 200 mg/kg, reduced the wear scar diameter of Diesel fuel b from 651 μm to 638 μm with almost no antiwear effect, indicating that diester compounds are not a good lubricity modifier, and the fatty acid-based lubricity modifier (Comparative Example I-3) and the fatty acid ester-based lubricity modifier (Comparative Example I-4) for diesel fuel only reduced the wear scar diameter of Diesel fuel b to 432 μm and 387 μm at a dosage of 200 mg/kg.

When the dosage is further reduced to 120 mg/kg or 100 mg/kg, the monoester compound of the present application can still enable the lubricity of the Diesel fuel b to meet the requirements of the diesel fuel standard; while the wear scar diameters of the Diesel fuel b are respectively reduced to 651 μm, 652 μm, 519 μm and 482 μm when the products of Comparative Examples I-1, I-2, I-3 and I-4 are added at a dosage of 120 mg/kg, which indicates a poor antiwear effect, and the criterion of no more than 460 μm required by the diesel fuel standard cannot be satisfied.

Test Example I-2

The test example compares the effects of the lubricity modifiers of the examples and the comparative examples when used in coal-based diesel fuel, wherein the lubricity modifiers are respectively mixed with coal-based Diesel fuel c, the Diesel fuel c is derived from direct coal liquefaction diesel fuel of China Shenhua Coal to Liquid and Chemical Co., Ltd., and its physicochemical properties are shown in Table I-5. The wear scar diameter WS1.4 of the diesel fuel after addition of the lubricity modifier as measured according to the HFRR method (ISO 12156-1) is shown in Table I-6.

TABLE I-5

Properties of Diesel fuel c

| Item | Diesel fuel c |
|---|---|
| Density (20° C.)/(kg · m$^{-3}$) | 837.9 |
| Initial boiling point/° C. | 187 |
| 5% temperature/° C. | 193 |
| 10% temperature/° C. | 197 |
| 20% temperature/° C. | 200 |
| 30% temperature/° C. | 202 |
| 50% temperature/° C. | 202 |
| 70% temperature/° C. | 213 |
| 90% temperature/° C. | 218 |
| 95% temperature/° C. | 229 |
| Final distillation point/° C. | 255 |
| Acidity/(mgKOH · 100 mL$^{-1}$) | 0.3 |
| Viscosity at 20° C./(mm$^2$ · s$^{-1}$) | 2.337 |
| Viscosity at 40° C./(mm$^2$ · s$^{-1}$) | 1.666 |
| 10% carbon residue, % | <0.05 |
| Oxidation stability, total insolubles (mg/100 mL) | <0.3 |
| Ash content, % | <0.002 |
| Cold filter plugging point/° C. | −50 |
| Freezing point/° C. | <−50 |
| Cetane number | 45 |
| Closed cup flash point/° C. | 63 |
| w (sulfur)/mg · L$^{-1}$ | 10 |
| Water content, % | Trace |
| Lubricity (HFRR)/μm | 663 |

TABLE I-6

Wear scar diameter WS1.4 of Diesel fuel c before and after addition of the lubricity modifier as measured according to the HFRR method (ISO 12156-1)

| Oil sample | Dosage of the modifier (mg·kg$^{-1}$) | WS1.4 (μm) |
|---|---|---|
| Diesel fuel c | / | 663 |
| Diesel fuel c + product of Example I-1 (monoisooctyl 1,2-cyclohexanedicarboxylate) | 180 | 304 |
| Diesel fuel c + product of Example I-1 (monoisooctyl 1,2-cyclohexanedicarboxylate) | 100 | 402 |
| Diesel fuel c + isooctanol | 180 | 638 |
| Diesel fuel c + product of Example I-2 (monoisononyl tetrahydrophthalate) | 180 | 308 |
| Diesel fuel c + product of Example I-2 (monoisononyl tetrahydrophthalate) | 100 | 410 |
| Diesel fuel c + isononanol | 180 | 643 |
| Diesel fuel c + product of Example I-3 (mono-p-nonylphenyl methyl-1,2-cyclohexanedicarboxylate) | 180 | 311 |
| Diesel fuel c + p-nonyl phenol | 180 | 649 |
| Diesel fuel c + product of Example I-4 (monobenzyl methyltetrahydrophthalate) | 180 | 291 |
| Diesel fuel c + benzyl alcohol | 180 | 647 |
| Diesel fuel c + Comparative Example I-1 (diisooctyl hexahydrophthalate) | 180 | 640 |
| Diesel fuel c + Comparative Example I-1 (diisooctyl hexahydrophthalate) | 100 | 657 |
| Diesel fuel c + Comparative Example I-2 (di-(2-ethylhexyl) phthalate) | 180 | 635 |
| Diesel fuel c + Comparative Example I-2 (di-(2-ethylhexyl) phthalate) | 100 | 653 |
| Diesel fuel c + Comparative Example I-3 (HiTEC 4140) | 180 | 433 |
| Diesel fuel c + Comparative Example I-3 (HiTEC 4140) | 100 | 499 |
| Diesel fuel c + Comparative Example I-4 (Infineum R655) | 180 | 398 |
| Diesel fuel c + Comparative Example I-4 (Infineum R655) | 100 | 503 |

From the results of the above test examples, it can be seen that the lubricity modifier of the present application is unexpectedly superior to the fatty acid-type or fatty acid ester-type lubricity modifiers, and, when used as a diesel lubricity modifier, the lubricity of low-sulfur diesel fuel can be remarkably improved and the addition amount can be greatly reduced.

The following Test Example II-1 compares the effects of lubricity modifiers according to the present application (Examples II-1 to II-20) and non-inventive lubricity modifiers (Comparative Examples II-1 to II-6) when used in diesel fuel, where the types and sources of the lubricity modifiers used are shown in the following Table II-1:

TABLE II-1

Types and sources of lubricity modifiers used in Test Example II-1

| Example No. | Type of the lubricity modifier | Source |
|---|---|---|
| Example II-1 | Monoisooctyl maleate | Purchased from Beijing Innochem Co., Ltd., with a purity of 95% |
| Example II-2 | Monolauryl maleate | Self-made |
| Example II-3 | Monoisononyl maleate (mono-2,6-dimethylheptan-4-yl maleate) | Self-made |
| Example II-4 | Mono-p-nonylphenyl maleate | Self-made |
| Example II-5 | Monobenzyl maleate | Self-made |
| Example II-6 | Monocyclohexyl maleate | Self-made |
| Example II-7 | Mono-3-cyclohexene-1-methyl maleate | Self-made |
| Example II-8 | Monobutyl maleate | Purchased from Tokyo Chemical Industry (TCI Shanghai), with a purity of 97% |
| Example II-9 | Monobutyl fumarate | Purchased from Tokyo Chemical Industry (TCI Shanghai), with a purity of 97% |
| Example II-10 | Monomethyl maleate | Purchased from Tokyo Chemical Industry (TCI Shanghai), with a purity of 95% |
| Example II-11 | Monoethyl maleate | Purchased from Aladdin Reagent Company, with a purity of 97% |
| Example II-12 | Monoisooctyl itaconate | Self-made |
| Example II-13 | Monolauryl itaconate | Self-made |
| Example II-14 | Monoisononyl itaconate | Self-made |
| Example II-15 | Mono-p-nonylphenyl itaconate | Self-made |
| Example II-16 | Monobenzyl itaconate | Self-made |
| Example II-17 | Monocyclohexyl itaconate | Self-made |
| Example II-18 | Monobutyl itaconate | Commercially available, with a purity of 99.5% |
| Example II-19 | Monoisooctyl citraconate (monoisooctyl methylmaleate) | Self-made |
| Example II-20 | Mono-7-methyl-1-octyl maleate | Self-made |
| Comparative Example II-1 | Monomethyl dodecenylsuccinate | Prepared as described in CN106929112A |
| Comparative Example II-2 | Diisooctyl maleate | Commercially available |
| Comparative Example II-3 | Fatty acid-based lubricity modifier HiTEC 4140 | Purchased from Afton Inc |
| Comparative Example II-4 | Fatty acid ester-based lubricity modifier Infineum R655 | Purchased from Infineum |

TABLE II-1-continued

Types and sources of lubricity modifiers used in Test Example II-1

| Example No. | Type of the lubricity modifier | Source |
|---|---|---|
| Comparative Example II-5 | Monobutyl dodecenylsuccinate | Prepared as described in CN106929112A |
| Comparative Example II-6 | Mono-2-ethylhexyl C20-24 alkenyl succinate | Prepared as described in CN106929112A |

The method for preparing the self-made lubricity modifiers listed in Table II-1 is described in detail hereinbelow:

Example II-2

215.6 g of maleic anhydride (with a mass fraction of 99.5%, available from Shanxi Qiaoyou chemical Co., Ltd.) and 372 g of lauryl alcohol (with a mass fraction of 99.9%, available under PALMAC, Malaysia) were charged into a 1000 mL reactor equipped with an electric stirrer, a thermometer and a reflux condenser, the molar ratio of maleic anhydride to lauryl alcohol was about 1.1:1, and the mixture was heated to 95° C. under stirring, reacted for 3 hours, then heated and distilled under reduced pressure to remove unreacted maleic anhydride, to obtain 581 g of monolauryl maleate. The reaction equation is as follows:

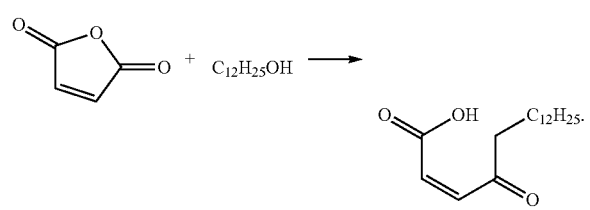

Example II-3

490 g of maleic anhydride (with a mass fraction of 99.5%, available from Zibo Qixiang Tengda Chemical Co., Ltd.) and 720 g of isononanol (Exxal™ 9s, 2,6-dimethyl-4-heptanol, with a mass fraction of 99.5%, available from Exxon-Mobil Co., Ltd.) were charged into a 2000 mL reactor equipped with an electric stirrer and a thermometer, the molar ratio of maleic anhydride to isononanol was about 1:1, and the mixture was heated under stirring to 85° C. and reacted for 5 hours, then heated and distilled under reduced pressure to remove unreacted isononanol and maleic anhydride, to obtain 1006 g of monoisononyl maleate (mono-2,6-dimethyl-4-heptyl maleate).

Example II-4

450 g of maleic anhydride (with a mass fraction of 99.5%, available from Shanghai Aladdin Biochemical Technology Co., Ltd.) and 910 g of p-nonylphenol (with a mass fraction of 98%, available from Huainan Kedi Chemical Technology Co., Ltd.) were charged into a 2000 mL reactor equipped with an electric stirrer and a thermometer, the molar ratio of maleic anhydride to p-nonylphenol was about 1:0.9, and the mixture was heated to 110° C. under stirring, reacted for 12 hours, then heated and distilled under reduced pressure to remove unreacted p-nonylphenol and maleic anhydride, to obtain 1296 g of mono-p-nonylphenyl maleate. The reaction equation is as follows:

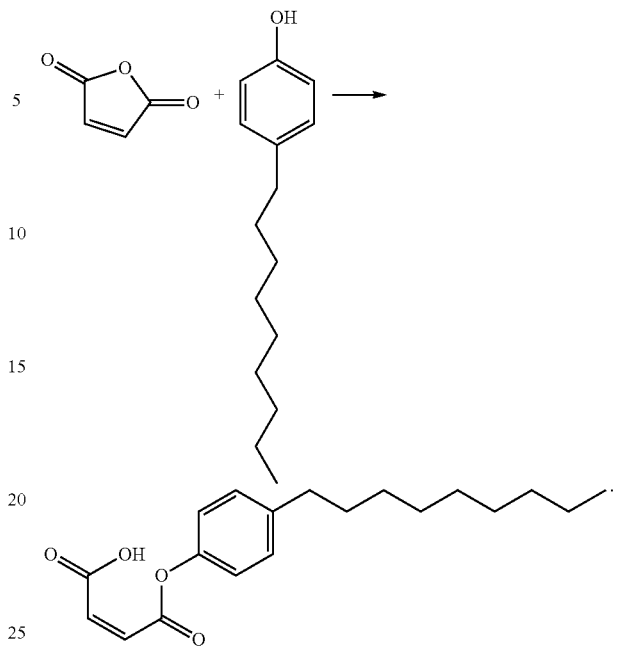

Example II-5

475 g of maleic anhydride (with a mass fraction of 99.5%, available from Shanghai Aladdin Biochemical Technology Co., Ltd.) and 796 g of benzyl alcohol (with a mass fraction of 99%, available from Shanghai Meryer chemical technology Co., Ltd.) were charged into a 2000 mL reactor equipped with an electric stirrer and a thermometer, the molar ratio of maleic anhydride to benzyl alcohol was about 1:1, the mixture was heated to 90° C. under stirring, reacted for 8 hours, then heated and distilled under reduced pressure to remove unreacted benzyl alcohol and maleic anhydride, to obtain 1196 g of monobenzyl maleate. The reaction equation is as follows:

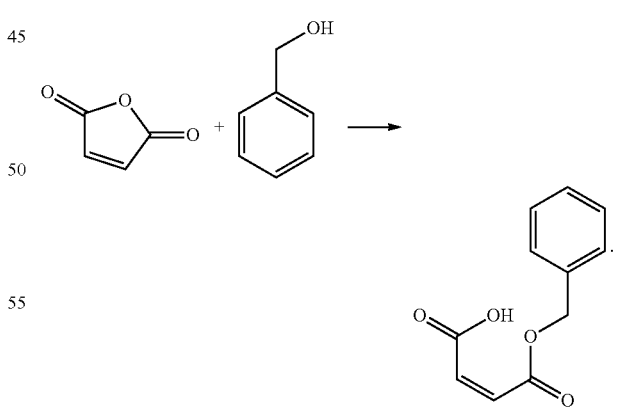

Example II-6

500 g of maleic anhydride (with a mass fraction of 99.5%, available from Beijing Innochem technology Co., Ltd.) and 665 g of cyclohexanol (with a mass fraction of 98%, available from Beijing Innochem technology Co., Ltd.) were charged into a 2000 mL reactor equipped with an electric stirrer and a thermometer, the molar ratio of maleic anhydride to cyclohexanol was about 1:1.3, the mixture was heated to 85° C. under stirring, reacted for 4 hours, then heated and distillated under reduced pressure to remove unreacted cyclohexanol and maleic anhydride, to obtain 1096 g of monocyclohexyl maleate. The reaction equation is as follows:

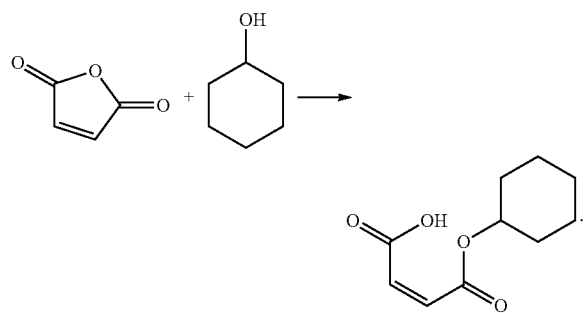

Example II-7

550 g of maleic anhydride (with a mass fraction of 99.5%, available from Beijing Innochem technology Co., Ltd.) and 504 g of 3-cyclohexene-1-methanol (with a mass fraction of 98%, available from Shanghai Bide Pharmatech Co., Ltd.) were charged into a 2000 mL reactor equipped with an electric stirrer and a thermometer, the molar ratio of maleic anhydride to 3-cyclohexene-1-methanol was about 1:0.8, and the mixture was heated under stirring to 75° C. and reacted for 6 hours, then heated and distillated under reduced pressure to remove unreacted 3-cyclohexene-1-methanol and maleic anhydride, to obtain 997 g of mono-3-cyclohexene-1-methyl maleate. The reaction equation is as follows:

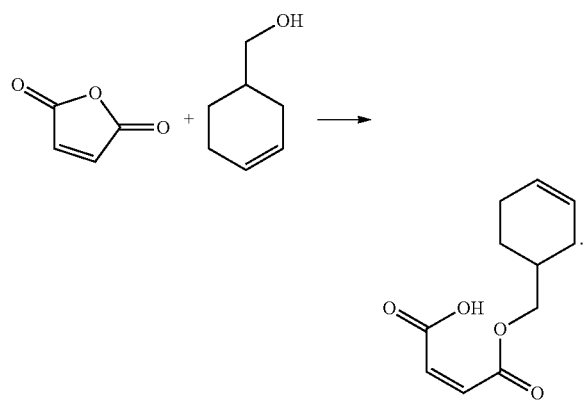

Example II-12

560 g of itaconic anhydride (with a mass fraction of 98%, available from Zhejiang Guoguang Biochemistry Co., Ltd.) and 650 g of isooctanol (2-ethylhexanol, with a mass fraction of 99.9%, available from Qilu Petrochemical Branch of Sinopec) were charged into a 2000 mL reactor equipped with an electric stirrer, a thermometer and a reflux condenser, the molar ratio of itaconic anhydride to isooctanol was about 1:1, the mixture was heated under stirring to 95° C. and reacted for 4 hours, then heated and distilled under reduced pressure to remove unreacted isooctanol and itaconic anhydride, to obtain 1193 g of monoisooctyl itaconate.

Example II-13

260 g of itaconic acid (with a mass fraction of 99.6%, available from Zhejiang Guoguang Biochemistry Co., Ltd.), 446 g of lauryl alcohol (with a mass fraction of 99.9%, available under PALMAC, Malaysia) and 7 g of p-toluenesulfonic acid were charged into a 1000 mL reactor equipped with an electric stirrer, a thermometer and a reflux condenser, the molar ratio of itaconic acid to lauryl alcohol was about 1.1:2, the mixture was heated to 165° C. under stirring, reacted for 6 hours, then heated and distilled under reduced pressure to remove unreacted raw materials, to obtain 611 g of monolauryl itaconate.

Example II-14

571 g of itaconic anhydride (with a mass fraction of 98%, available from Zhejiang Guoguang Biochemistry Co., Ltd.) and 792 g of isononanol (Exxal™ 9s, with a mass fraction of 99.5%, available from Exxon-Mobil Co., Ltd.) into a 2000 mL reactor equipped with an electric stirrer and a thermometer, the molar ratio of itaconic anhydride to isononanol was about 1:1.1, heated to 90° C. under stirring, reacted for 5 hours, then heated and distilled under reduced pressure to remove unreacted isononanol and itaconic anhydride, to obtain 1286 g of monoisononyl itaconate.

Example II-15

56 g of itaconic anhydride (with a mass fraction of 97%, available from Aladdin Reagent) and 121 g of nonylphenol (with a mass fraction of 99.5%, available from CMMFC, Taiwan), into a 500 mL reactor equipped with an electric stirrer, a thermometer and a reflux condenser, the molar ratio of itaconic anhydride to nonylphenol was about 1.1:1, heated under stirring to 100° C., and reacted for 5.5 hours, to obtain 171 g of a mixture mainly comprising mono-p-nonylphenyl itaconate.

Example II-16

490 g of itaconic anhydride (with a mass fraction of 95%, available from Tokyo Chemical Industry, Japan) and 540 g of benzyl alcohol (with a mass fraction of 99.5%, available from Shandong Luxi Group Co., Ltd.) were charged into a 2000 mL reactor equipped with an electric stirrer and a thermometer, the molar ratio of itaconic anhydride to benzyl alcohol was about 1:1, the mixture was heated to 100° C. under stirring, and reacted for 4.5 hours, then heated and distilled under reduced pressure to remove unreacted benzyl alcohol and itaconic anhydride, to obtain 996 g of monobenzyl itaconate.

Example II-17

147 g of itaconic anhydride (with a mass fraction of 97%, available from Aladdin Reagent) and 180 g of cyclohexanol (with a mass fraction of 98%, available from Aladdin Reagent) were charged into a 500 mL reactor with an electric stirrer, a thermometer and a reflux condenser, the molar ratio of itaconic anhydride to cyclohexanol was about 1.1:1, the mixture was heated under stirring to 80° C., reacted for 6 hours, and then heated and distilled under reduced pressure to remove unreacted cyclohexanol, to obtain 296 g of monocyclohexyl itaconate.

Example II-19

150 g of citraconic anhydride (with a mass fraction of 98%, available from TCI Shanghai) and 192 g of isooctanol (2-ethylhexanol, with a fraction of 99.9%, available from Qilu Petrochemical Branch of Sinopec) were charged into a 500 mL reactor equipped with an electric stirrer, a thermometer and a reflux condenser, the molar ratio of citraconic anhydride to isooctanol was about 1.1:1, and the mixture was heated under stirring to 75° C., reacted for 8 hours, and distilled under reduced pressure to remove unreacted isooctanol, to obtain 329 g of monoisooctyl citraconate. The reaction equation is as follows:

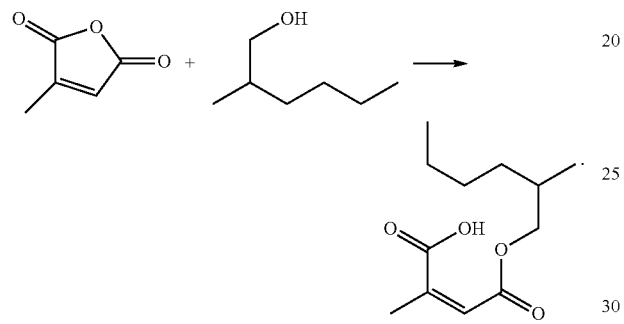

Example II-20

196 g of maleic anhydride (with a mass fraction of 99.5%, available from Shanghai Aladdin Biochemical Technology Co., Ltd.) and 316.8 g of 7-methyl-1-octanol (with a mass fraction of 99%, available from Hubei Wanye Pharmaceutical Co., Ltd.) were charged into a 1000 mL reactor equipped with an electric stirrer and a thermometer, the molar ratio of maleic anhydride to 7-methyl-1-octanol was about 1:1.1, the mixture was heated under stirring to 90° C. and reacted for 4 hours, to obtain 498 g of a product mainly comprising mono-7-methyl-1-octyl maleate.

Test Example II-1

This test example compares the effects of the lubricity modifiers of examples and comparative examples when used in diesel fuel, in which the lubricity modifiers were mixed with Diesel fuel a and Diesel fuel b shown in Table I-2, respectively. The wear scar diameter WS1.4 of the diesel fuel before and after addition of the lubricity modifier is shown in Tables II-2 and II-3, in which the smaller the wear scar diameter, the better the lubricity of the diesel fuel is.

TABLE II-2

Wear scar diameter WS1.4 of Diesel fuel a before and after addition of the lubricity modifier as mearsued according to HFRR method

| Oil sample | Dosage of the modifier ($mg \cdot kg^{-1}$) | WS1.4 ($\mu m$) |
|---|---|---|
| Diesel fuel a | / | 564 |
| Diesel fuel a + product of Example II-1 (monoisooctyl maleate) | 150 | 211 |
| Diesel fuel a + product of Example II-1 (monoisooctyl maleate) | 80 | 312 |
| Diesel fuel a + product of Example II-2 (monolauryl maleate) | 150 | 205 |
| Diesel fuel a + product of Example II-2 (monolauryl maleate) | 80 | 309 |
| Diesel fuel a + product of Example II-3 (monoisononyl maleate) | 150 | 215 |
| Diesel fuel a + product of Example II-3 (monoisononyl maleate) | 80 | 310 |
| Diesel fuel a + product of Comparative Example II-4 (mono-p-nonylphenyl maleate) | 150 | 301 |
| Diesel fuel a + product of Comparative Example II-4 (mono-p-nonylphenyl maleate) | 80 | 399 |
| Diesel fuel a + product of Example II-5 (monobenzyl maleate) | 150 | 268 |
| Diesel fuel a + product of Example II-5 (monobenzyl maleate) | 80 | 365 |
| Diesel fuel a + product of Example II-6 (monocyclohexyl maleate) | 150 | 303 |
| Diesel fuel a + product of Example II-6 (monocyclohexyl maleate) | 80 | 387 |
| Diesel fuel a + product of Example II-7 (mono-3-cyclohexene-1-methyl maleate) | 150 | 255 |
| Diesel fuel a + product of Example II-7 (mono-3-cyclohexene-1-methyl maleate) | 80 | 373 |
| Diesel fuel a + product of Example II-8 (monobutyl maleate) | 150 | 219 |
| Diesel fuel a + product of Example II-8 (monobutyl maleate) | 80 | 376 |
| Diesel fuel a + product of Example II-9 (monobutyl fumarate) | 150 | 315 |
| Diesel fuel a + product of Example II-9 (monobutyl fumarate) | 80 | 401 |
| Diesel fuel a + product of Example II-10 (monomethyl maleate) | 150 | 256 |
| Diesel fuel a + product of Example II-10 (monomethyl maleate) | 80 | 321 |
| Diesel fuel a + product of Example II-11 (monoethyl maleate) | 150 | 225 |

TABLE II-2-continued

Wear scar diameter WS1.4 of Diesel fuel a before and after addition of the lubricity modifier as mearsued according to HFRR method

| Oil sample | Dosage of the modifier (mg · kg⁻¹) | WS1.4 (μm) |
|---|---|---|
| Diesel fuel a + product of Example II-11 (monoethyl maleate) | 80 | 331 |
| Diesel fuel a + product of Example II-12 (monoisooctyl itaconate) | 150 | 221 |
| Diesel fuel a + product of Example II-12 (monoisooctyl itaconate) | 80 | 345 |
| Diesel fuel a + product of Example II-13 (monolauryl itaconate) | 150 | 219 |
| Diesel fuel a + product of Example II-13 (monolauryl itaconate) | 80 | 332 |
| Diesel fuel a + product of Example II-14 (monoisononyl itaconate) | 150 | 218 |
| Diesel fuel a + product of Example II-14 (monoisononyl itaconate) | 80 | 345 |
| Diesel fuel a + product of Comparative Example II-15 (mono-p-nonylphenyl itaconate) | 150 | 298 |
| Diesel fuel a + product of Comparative Example II-15 (mono-p-nonylphenyl itaconate) | 80 | 391 |
| Diesel fuel a + product of Example II-16 (monobenzyl itaconate) | 150 | 297 |
| Diesel fuel a + product of Example II-16 (monobenzyl itaconate) | 80 | 390 |
| Diesel fuel a + product of Example II-17 (monocyclohexyl itaconate) | 150 | 301 |
| Diesel fuel a + product of Example II-17 (monocyclohexyl itaconate) | 80 | 400 |
| Diesel fuel a + product of Example II-18 (monobutyl itaconate) | 150 | 297 |
| Diesel fuel a + product of Example II-18 (monobutyl itaconate) | 80 | 393 |
| Diesel fuel a + product of Example II-19 (monoisooctyl methylmaleate) | 150 | 381 |
| Diesel fuel a + product of Example II-19 (monoisooctyl methylmaleate) | 80 | 458 |
| Diesel fuel a + Comparative Example II-1 (monomethyl dodecenylsuccinate) | 150 | 398 |
| Diesel fuel a + Comparative Example II-1 (monomethyl dodecenylsuccinate) | 80 | 467 |
| Diesel fuel a + Comparative Example II-2 (diisooctyl maleate) | 150 | 560 |
| Diesel fuel a + Comparative Example II-3 (HiTEC 4140) | 150 | 427 |
| Diesel fuel a + Comparative Example II-3 (HiTEC 4140) | 80 | 499 |
| Diesel fuel a + Comparative Example II-4 (Infineum R655) | 150 | 394 |
| Diesel fuel a + Comparative Example II-4 (Infineum R655) | 80 | 491 |

TABLE II-3

Wear scar diameter WS1.4 of Diesel fuel b before and after addition of the lubricity modifier as measured according to HFRR method

| Oil sample | Dosage of the modifier (mg · kg⁻¹) | WS1.4 (μm) |
|---|---|---|
| Diesel fuel b | / | 651 |
| Diesel fuel b + product of Example II-1 (monoisooctyl maleate) | 200 | 208 |
| Diesel fuel b + product of Example II-1 (monoisooctyl maleate) | 120 | 349 |
| Diesel fuel b + product of Example II-2 (monolauryl maleate) | 200 | 206 |
| Diesel fuel b + product of Example II-2 (monolauryl maleate) | 100 | 397 |
| Diesel fuel b + lauryl alcohol | 200 | 628 |
| Diesel fuel b + product of Example II-3 (monoisononyl maleate) | 200 | 233 |
| Diesel fuel b + product of Example II-3 (monoisononyl maleate) | 120 | 338 |
| Diesel fuel b + product of Comparative Example II-4 (mono-p-nonylphenyl maleate) | 200 | 292 |
| Diesel fuel b + product of Comparative Example II-4 (mono-p-nonylphenyl maleate) | 120 | 391 |
| Diesel fuel b + product of Example II-5 (monobenzyl maleate) | 200 | 241 |
| Diesel fuel b + product of Example II-5 (monobenzyl maleate) | 100 | 415 |
| Diesel fuel b + product of Example II-6 (monocyclohexyl maleate) | 200 | 300 |
| Diesel fuel b + product of Example II-6 (monocyclohexyl maleate) | 120 | 402 |
| Diesel fuel b + product of Example II-7 (mono-3-cyclohexene-1-methyl maleate) | 200 | 291 |
| Diesel fuel b + product of Example II-7 (mono-3-cyclohexene-1-methyl maleate) | 120 | 395 |

TABLE II-3-continued

Wear scar diameter WS1.4 of Diesel fuel b before and after addition of the lubricity modifier as measured according to HFRR method

| Oil sample | Dosage of the modifier (mg · kg$^{-1}$) | WS1.4 (μm) |
|---|---|---|
| Diesel fuel b + product of Example II-8 (monobutyl maleate) | 200 | 302 |
| Diesel fuel b + product of Example II-8 (monobutyl maleate) | 120 | 410 |
| Diesel fuel b + product of Example II-9 (monobutyl fumarate) | 200 | 353 |
| Diesel fuel b + product of Example II-9 (monobutyl fumarate) | 120 | 420 |
| Diesel fuel b + product of Example II-10 (monomethyl maleate) | 200 | 243 |
| Diesel fuel b + product of Example II-10 (monomethyl maleate) | 120 | 341 |
| Diesel fuel b + product of Example II-11 (monoethyl maleate) | 200 | 237 |
| Diesel fuel b + product of Example II-11 (monoethyl maleate) | 120 | 329 |
| Diesel fuel b + product of Example II-12 (monoisooctyl itaconate) | 200 | 235 |
| Diesel fuel b + product of Example II-12 (monoisooctyl itaconate) | 120 | 367 |
| Diesel fuel b + product of Example II-13 (monolauryl itaconate) | 200 | 289 |
| Diesel fuel b + product of Example II-13 (monolauryl itaconate) | 100 | 401 |
| Diesel fuel b + product of Example II-14 (monoisononyl itaconate) | 200 | 245 |
| Diesel fuel b + product of Example II-14 (monoisononyl itaconate) | 120 | 387 |
| Diesel fuel b + product of Comparative Example II-15 (mono-p-nonylphenyl itaconate) | 200 | 301 |
| Diesel fuel b + product of Comparative Example II-15 (mono-p-nonylphenyl itaconate) | 120 | 412 |
| Diesel fuel b + product of Example II-16 (monobenzyl itaconate) | 200 | 291 |
| Diesel fuel b + product of Example II-16 (monobenzyl itaconate) | 100 | 412 |
| Diesel fuel b + product of Example II-17 (monocyclohexyl itaconate) | 200 | 302 |
| Diesel fuel b + product of Example II-17 (monocyclohexyl itaconate) | 120 | 411 |
| Diesel fuel b + product of Example II-18 (monobutyl itaconate) | 200 | 298 |
| Diesel fuel b + product of Example II-18 (monobutyl itaconate) | 120 | 386 |
| Diesel fuel b + product of Example II-19 (monoisooctyl methylmaleate) | 200 | 319 |
| Diesel fuel b + product of Example II-19 (monoisooctyl methylmaleate) | 120 | 420 |
| Diesel fuel b + product of Example II-20 (mono-7-methyl-1-octyl maleate) | 200 | 235 |
| Diesel fuel b + product of Example II-20 (mono-7-methyl-1-octyl maleate) | 120 | 336 |
| Diesel fuel b + Comparative Example II-1 (monomethyl dodecenylsuccinate) | 200 | 389 |
| Diesel fuel b + Comparative Example II-1 (monomethyl dodecenylsuccinate) | 120 | 471 |
| Diesel fuel b + Comparative Example II-2 (diisooctyl maleate) | 200 | 639 |
| Diesel fuel b + Comparative Example II-3 (HiTEC 4140) | 200 | 432 |
| Diesel fuel b + Comparative Example II-3 (HiTEC 4140) | 120 | 519 |
| Diesel fuel b + Comparative Example II-4 (Infineum R655) | 200 | 387 |
| Diesel fuel b + Comparative Example II-4 (Infineum R655) | 120 | 482 |
| Diesel fuel b + Comparative Example II-5 (monobutyl dodecenylsuccinate) | 200 | 412 |
| Diesel fuel b + Comparative Example II-5 (monobutyl dodecenylsuccinate) | 120 | 503 |
| Diesel fuel b + Comparative Example II-6 (mono-2-ethylhexyl C20-24 alkenyl succinate) | 200 | 423 |
| Diesel fuel b + Comparative Example II-6 (mono-2-ethylhexyl C20-24 alkenyl succinate) | 120 | 522 |

As can be seen from Tables II-2 and II-3, the lubricity of the diesel fuel is substantially not improved by the addition of an alcohol compound such as lauryl alcohol, whereas the lubricity of the diesel fuel is surprisingly greatly improved by the addition of an unsaturated dicarboxylic acid monoester-based compound of the present application.

For the low sulfur diesel fuel shown in Table II-2, the unsaturated dicarboxylic acid monoester compound of the present application greatly improves the lubricity of the diesel fuel even at a very small dosage. For example, the monoesters of Examples II-1 and II-2 can reduce the wear scar diameter of Diesel fuel a from 564 μm to 211 μm and 205 μm at a dosage of 150 mg/kg. In contrast, monomethyl dodecenylsuccinate of Comparative Example II-1 can only reduce the wear scar diameter to 398 μm, and diisooctyl maleate of Comparative Example II-2 has no effect of improving the lubricity of the diesel fuel; even the fatty acid-based lubricity modifier (Comparative Example II-3) and fatty acid ester-based lubricity modifier (Comparative Example II-4) for diesel fuel commonly used in industry at present can only reduce the wear scar diameter of Diesel fuel a to 427 µm and 394 µm at dosage of 150 mg/kg. It can be seen that the unsaturated dicarboxylic acid monoester compounds of the present application show very excellent antiwear effects. When the dosage is further reduced to 80 mg/kg, the unsaturated dicarboxylic acid monoester compound of the present application can still enable the lubricity of the Diesel fuel a to meet the requirements of the diesel fuel standard, and the antiwear effect of the products of the comparative examples is too poor at such a dosage to meet the requirement of the diesel fuel standard of no more than 460 µm.

For the ultra-low sulfur diesel fuel shown in Table II-3, the unsaturated dicarboxylic acid monoester compounds of the present application surprisingly improve the lubricity of diesel fuel at a very low dosage. For example, it is surprising that the wear scar diameter of Diesel fuel b is reduced from 651 µm to 208 µm and 206 µm using the monoesters of Examples II-1 and II-2 at a dosage of 200 mg/kg.

The monomethyl dodecenylsuccinate of Comparative Example II-1 can only reduce the wear scar diameter of Diesel fuel b from 651 µm to 389 µm at a dosage of 200 mg/kg, and the fatty acid-based lubricity modifier (Comparative Example II-3) and fatty acid ester-based lubricity modifier (Comparative Example II-4) for diesel fuel can only reduce the wear scar diameter of Diesel fuel b to 432 µm and 387 µm at 200 mg/kg. When the dosage is further reduced to 120 mg/kg, the unsaturated dicarboxylic acid monoester compound of the present application can still enable the lubricity of the Diesel fuel b to meet the requirements of the diesel fuel standard, while the wear scar diameters of the Diesel fuel b can only be reduced to 471 µm, 519 µm and 482 µm using the products of Comparative Examples II-1, II-3 and II-4 at a dosage of 120 mg/kg, indicating a poor antiwear effect, which is not sufficient to enable the diesel fuel to meet the lubricity requirement of the diesel fuel standard of no more than 460 µm. Comparison of the effects of Comparative Examples II-5 and II-6 with those of Examples II-8 and II-1, respectively, further reveals that the antiwear effect of a dicarboxylic acid monoester having a long-chain substituent is significantly deteriorated.

It can also be seen from Test Example II-1 that the preferred maleic acid monoesters and itaconic acid monoesters are more effective in improving the lubricity of diesel fuel, while fumaric acid monoesters having a trans-structure and methyl maleic acid monoesters having a side chain are slightly less effective.

The following Test Example III-1 compares the effects of lubricity modifiers according to the present application (Examples III-1 to III-3) and non-inventive lubricity modifiers (Comparative Examples III-1 to III-3) when used in aviation fuels, in which the types and sources of lubricity modifiers used are shown in Table III-1 below:

TABLE III-1

Types and sources of lubricity modifiers used in Test Example III-1

| Example No. | Type of the lubricity modifier | Source |
|---|---|---|
| Example III-1 | Monoisooctyl maleate | Purchased from TCI Shanghai, with a purity of 95% |
| Example III-2 | Monobutyl maleate | Purchased from Hubei Jusheng Technologies, Inc., with a purity of 99% |
| Example III-3 | Monoisodecyl maleate | Self-made |
| Comparative Example III-1 | T1602 naphthenic acid lubricity modifier | Purchased from Hunan Xingchang Company |
| Comparative Example III-2 | Dimer acid lubricity modifier | Purchased from Xinjiang Dasen Chemical Co., Ltd. |
| Comparative Example III-3 | Monoisononyl dodecenylsuccinate | Self-made |

The method for preparing the self-made lubricity modifiers listed in Table III-1 is described in detail hereinbelow:

Example III-3

50 g of maleic anhydride (available from Shanghai Aladdin Biochemical Technology Co., Ltd.) and 104.9 g of isodecanol (obtained from Shanghai Aladdin Biochemical Technology Co., Ltd.) were weighed and charged into a three-neck flask reactor equipped with a stirrer, a thermometer and a reflux condenser. The mixture was reacted for 3 hours at 90° C., and cooled to room temperature, to obtain a product mainly comprising monoisodecyl maleate product.

Comparative Example III-3

100 g of dodecenyl succinic anhydride (available from Shanghai Aladdin Biochemical Technology Co., Ltd.) and 70.4 g of isononanol (available from Shanghai Aladdin Biochemical Technology Co., Ltd.) were weighed and charged into a three-neck flask reactor equipped with a stirrer, a thermometer and a reflux condenser. The mixture was reacted for 3 hours at 140° C., and cooled to room temperature, to obtain a product mainly comprising monoisononyl dodecenylsuccinate.

Test Example III-1

This test example compares the effects of the lubricity modifiers of examples and comparative examples when used in aviation fuels, of which the physicochemical properties are shown in Table III-2. The lubricity modifiers shown were added to the aviation fuels, respectively, and the wear scar diameter of the aviation fuel after addition of the lubricity modifiers was measured in accordance with SH/T0687 (ASTM D5001). The water reactivity and water separation index of the aviation fuel after addition of the lubricity modifier were measured according to methods GB/T1793 and SH/T0616, and the results are shown in Table III-3.

TABLE III-2

Properties of the aviation fuel used in Example III-1

| Items | Test results | Analytical method |
|---|---|---|
| Appearance | Qualified | Visual inspection |
| Colour(s) | +30 | GB/T 3555-1992 (2004) |
| Total acid number/(mgKOH/g) | 0.001 | GB/T 12574-1990 (2004) |
| Aromatic hydrocarbon content (volume fraction)/% | 10.4 | GB/T 11132-2008 |
| Olefin content (volume fraction)/% | 1.0 | |
| Total sulfur content (mass fraction)/% | 0.0001 | NB/SH/T 0842-2010 |
| Mercaptan sulfur (mass fraction)/% | <0.0003 | GB/T 1792-2015 |

TABLE III-2-continued

Properties of the aviation fuel used in Example III-1

| Items | Test results | Analytical method |
|---|---|---|
| Distillation range | | GB/T 6536-2010 |
| Initial boiling point/° C. | 158.5 | |
| 10% recovery temperature/° C. | 172.4 | |
| 20% recovery temperature/° C. | 179.2 | |
| 50% recovery temperature/° C. | 201.7 | |
| 90% recovery temperature/° C. | 240.7 | |
| Final distillation point/° C. | 261.1 | |
| Residual amount (volume fraction)/% | 1.1 | |
| Amount of loss (volume fraction)/% | 0.6 | |
| Flash point/° C. | 45.0 | GB/T 21789-2008 |
| Density (20° C.)/(kg/m$^3$) | 810.0 | SH/T 0604-2000 |
| Freezing point/° C. | −64.9 | SH/T 0770-2005 |
| Net calorific value/(MJ/kg) | 43.19 | GB/T 384-1981(2004) |
| Smoke point/mm | 26.7 | GB/T 382-2017 |
| Copper strip corrosion (100° C., 2 h)/grade | 1a | GB/T 5096-1985(2004) |
| Viscosity/(mm$^2$/s) 20° C. | 1.822 | GB/T 265-1988(2004) |
| Viscosity/(mm$^2$/s) −20° C. | 4.459 | GB/T 265-1988(2004) |
| Smoke point/mm | 26.7 | GB/T 382-2017 |
| Silver strip corrosion (50° C., 4 h)/grade | 0 | SH/T 0023-1990(2006) |
| Thermal stability (260° C., 2.5 h) | | GB/T 9169-2010 |
| Pressure drop/kPa | 0 | |
| Tube color rating/grade | 0 | |
| Existent gum/(mg/100 mL) | <1 | GB/T 8019-2008 |
| Water reactivity | | GB/T 1793-2008 |
| Interface condition/grade | 1b | |
| Degree of separation/grade | 2 | |
| Water separation index | 99 | SH/T 0616-1995(2004) |
| Wear scar diameter/mm | 0.87 | SH/T 0687-2000(2007) |

TABLE III-3

Test results of Test Example III-1

| Lubricity modifiers | Dosage/ (mg/L) | Wear scar diameter/ mm | Water reactivity, interface condition/ grade | Water reactivity, degree of separation/ grade | Water separation index |
|---|---|---|---|---|---|
| Example III-1 (monoisooctyl maleate) | 15 | 0.58 | 1b | 2 | 96 |
| | 20 | 0.54 | 1b | 2 | 95 |
| Example III-2 (monobutyl maleate) | 15 | 0.59 | 1b | 2 | 95 |
| | 20 | 0.55 | 1b | 2 | 92 |
| Example III-3 (monoisodecyl maleate) | 15 | 0.60 | 1b | 2 | 96 |
| | 20 | 0.56 | 1b | 2 | 94 |
| Comparative Example III-1 (naphthenic acid lubricity modifier) | 15 | 0.60 | 1b | 2 | 95 |
| | 20 | 0.57 | 1b | 2 | 94 |
| Comparative Example III-2 (dimer acid lubricity modifier) | 15 | 0.61 | 1b | 2 | 96 |
| | 20 | 0.58 | 1b | 2 | 95 |
| Comparative Example III-3 (monoisononyl dodecenylsuccinate) | 15 | 0.81 | 1b | 2 | 92 |
| | 20 | 0.76 | 1b | 2 | 90 |

As can be seen from Table III-3, the dicarboxylic acid monoester lubricity modifiers of the present application provide superior improvement in the lubricity of aviation fuel over the comparative examples, and the results of the water reactivity and water separation index tests are comparable to those of the lubricity modifier for aviation fuel of the comparative examples.

The following Test Example IV-1 compares the effects of the lubricity modifiers according to the present application (Examples IV-1 to IV-4) and the non-inventive lubricity modifiers (Comparative Examples IV-1 to IV-4) when used in gasoline, in which the types and sources of the lubricity modifiers used are shown in the following Table IV-1:

TABLE IV-1

Types and sources of lubricity modifiers used in Test Example IV-1

| Example No. | Type of the lubricity modifier | Source |
|---|---|---|
| Example IV-1 | Monoisooctyl maleate (mono-2-ethylhexyl maleate) | Purchased from TCI Shanghai, with a purity of more than 90% |
| Example IV-2 | Monobutyl maleate | Purchased from Hubei Jusheng Technologies, Inc., with a purity of 99% |
| Example IV-3 | Monoethyl maleate | Purchased from Shanghai Aladdin Biochemical Technology Co., Ltd., with a purity of 95% |
| Example IV-4 | Monoisooctyl methyltetrahydrophthalate | Commercially available |
| Comparative Example IV-1 | Fatty acid-based lubricity modifier JC-2006S | Purchased from Jiangsu Innovation Petrochemical Co., Ltd. |
| Comparative Example IV-2 | Fatty glyceride-based lubricity modifier JC-2017Z | Purchased from Jiangsu Innovation Petrochemical Co., Ltd. |
| Comparative Example IV-3 | Gasoline detergent with polyether amine as main agent | Commercially available, Syngnathus Fuel oil treasure |
| Comparative Examples IV-4 | Diisooctyl maleate | Purchased from Shanghai Aladdin Biochemical Technology Co., Ltd., with a purity of 95% |

Test Example IV-1

Test Example IV-1 compares the effects of the lubricity modifiers of the examples and comparative examples when used in gasoline, in which the lubricity modifiers were blended with gasoline, respectively, and the physicochemical properties of the ethanol gasoline for motor vehicles (E10) and the motor gasoline used are shown in Table IV-2. The wear scar diameter (WSD) of gasoline at 25° C. was measured on a High-Frequency lubricating Rig (HFRR, PCS instruments, UK), and the smaller the wear scar diameter, the better the lubricity of the gasoline or the better the effect of the lubricity modifier, and the results are shown in

TABLE IV-2

Properties of the gasoline used in Example IV-1

| Item | 92# Ethanol gasoline for motor vehicles (E10) | 95# Motor gasoline |
|---|---|---|
| Research Octane Number (RON) | 95.0 | 96.0 |
| Motor Octane Number (MON) | 83.8 | 86.6 |
| Volume fraction of aromatic hydrocarbons/% | 32.1 | 25.8 |

TABLE IV-2-continued

Properties of the gasoline used in Example IV-1

| Item | 92# Ethanol gasoline for motor vehicles (E10) | 95# Motor gasoline |
|---|---|---|
| Volume fraction of olefins/% | 8.7 | 6.8 |
| Volume fraction of saturated hydrocarbons/% | 59.2 | 67.4 |
| Vapor Pressure (RVPE)/kPa | 55.6 | 54.1 |
| Net calorific value/(MJ/k g) | 41.5 | 42.25 |
| Distillation range/° C. | | |
| Initial boiling point | 38.0 | 25.73 |
| T10 | 53.9 | 56.9 |
| T20 | 59.4 | 68.11 |
| T30 | 64.3 | 79.1 |
| T40 | 68.1 | 91.47 |
| T50 | 99.0 | 104.22 |
| T60 | 116.2 | 115.23 |
| T70 | 132.5 | 124.5 |
| T80 | 147.2 | 136.64 |
| T90 | 163.7 | 156.52 |
| T95 | 174.5 | 171.24 |
| Final distillation point | 194.0 | 193.52 |
| Residual amount/% (φ) | 0.6 | 0.5 |
| Amount of loss/% (φ) | 2.0 | 2 |
| Density at 20° C./(kg/m$^3$) | 749.2 | 739.5 |
| Density at 15° C./(kg/m$^3$) | 753.7 | 743.6 |
| Carbon content/% (w) | 86.8 | 86.43 |
| Hydrogen content/% (w) | 13.2 | 13.57 |
| Gum (unwashed)/(mg/100 mL) | 1.3 | 13.1 |
| Gum (after washing)/(mg/100 mL) | <0.5 | <0.5 |
| Benzene content/% (w) | 0.6 | 0.3 |
| Toluene/% (w) | 5.2 | 6.95 |
| Ethanol/% (w) | 11.0 | 0 |
| MTBE/% (w) | 0 | 6.16 |
| Mercaptan sulfur/(mg/kg) | <3 | <3 |
| Water soluble acids or bases | None | None |
| Copper strip corrosion (50° C., 3 h)/grade | 1a | 1a |
| Fe content/(mg/kg) | <1 | <1 |
| Pb content/(mg/kg) | 1.5 | <1 |
| P content/(mg/kg) | <1 | <1 |
| Si content/(mg/kg) | <1 | <1 |
| Mn content/(mg/kg) | <1 | <1 |
| Chlorine content/(mg/L) | 0.4 | 0.65 |
| Water content/(mg/L) | 1039.0 | 76 |
| Sulfur content/(mg/L) | 2.7 | 4.5 |
| Induction period/min | >1000 | >1000 |
| Nitrogen content/(mg/L) | 57.0 | 11 |
| Diene value/(gI$_2$/100 g) | 1.1 | 1.2 |

TABLE IV-3

Test results of Test Example IV-1

| Oil sample | Dosage (mg · kg$^{-1}$) | WSD (μm) |
|---|---|---|
| 92# Ethanol gasoline for motor vehicles (E10) | / | 848 |
| E10 + product of Example IV-1 (monoisooctyl maleate) | 150 | 378 |
| E10 + product of Example IV-1 (monoisooctyl maleate) | 200 | 296 |
| E10 + product of Example IV-2 (monobutyl maleate) | 200 | 312 |
| E10 + product of Example IV-3 (monoethyl maleate) | 200 | 325 |
| E10+ product of Example IV-4 (monooctyl methyltetrahydrophthalate) | 200 | 328 |
| E10 + Comparative Example IV-1 | 200 | 533 |
| E10 + Comparative Example IV-2 | 200 | 489 |
| E10 + Comparative Example IV-4 | 200 | 822 |
| 95# Motor gasoline | / | 843 |
| 95# Motor gasoline + product of Example IV-1 (monoisooctyl maleate) | 180 | 303 |
| 95# Motor gasoline + product of Example IV-2 (monobutyl maleate) | 180 | 317 |
| 95# Motor gasoline + product of Example IV-3 (monoethyl maleate) | 180 | 325 |
| 95# Motor gasoline + product of Example IV-4 (monooctyl methyltetrahydrophthalate) | 180 | 384 |
| 95# Motor gasoline + Comparative Example IV-1 | 180 | 598 |
| 95# Motor gasoline + Comparative Example IV-2 | 180 | 502 |
| 95# Motor gasoline + Comparative Example IV-3 | 180 | 786 |

As can be seen from Table IV-3, the wear scar diameters of blank 92 # Ethanol gasoline for motor vehicles (E10) and 95 # Motor gasoline measured using the HFRR tester at 25° C. are respectively as high as 848 μm and 843 μm, the lubricity of the gasoline can be greatly improved by adding the dicarboxylic acid monoester lubricity modifier of the present application. The monoester of Example IV-1 can reduce the wear scar diameter of 92 # Ethanol gasoline for motor vehicles (E10) to 378 μm when added at a dosage of 150 mg/kg, and can reduce the wear scar diameter of 92 # Ethanol gasoline for motor vehicles (E10) to 296 μm when added at a dosage of 200 mg/kg; which effect is far better than that of the fatty acid-based and fatty glyceride-based lubricity modifiers used in the industry at present, such as those of Comparative Example IV-1 and Comparative Example IV-2, by which the wear scar diameter can only be reduced to 533 μm and 498 μm, respectively, when used at a dosage of 200 mg/kg. The dicarboxylic acid diester compound such as plasticizer diisooctyl maleate (Comparative Example IV-4) has little effect of improving the lubricity of gasoline, and can only reduce the wear scar diameter of 92 # Ethanol gasoline for motor vehicles (E10) to 822 μm when added at a dosage of 200 mg/kg. The effect of gasoline detergent on improving the lubricity of gasoline is not significant either. For example, the product of Comparative Example IV-3 can only reduce the wear scar diameter of 95 # Motor gasoline to 786 μm when added at a dosage of 180 mg/kg.

The present application is illustrated in detail hereinabove with reference to preferred embodiments, but is not intended to be limited to those embodiments. Various modifications may be made following the inventive concept of the present application, and these modifications shall be within the scope of the present application.

It should be noted that the various technical features described in the above embodiments may be combined in any suitable manner without contradiction, and in order to avoid unnecessary repetition, various possible combinations are not described in the present application, but such combinations shall also be within the scope of the present application.

In addition, the various embodiments of the present application can be arbitrarily combined as long as the combination does not depart from the spirit of the present application, and such combined embodiments should be considered as the disclosure of the present application.

The invention claimed is:

1. A fuel composition, comprising a fuel component and a lubricity modifier comprising a dicarboxylic acid monoester compound of formula (I):

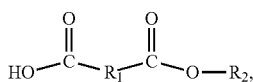

wherein $R_1$ represents a unsubstituted $C_{2-6}$ divalent alkenyl group or a group of formula —$R_3$—$R_4$—$R_5$—;
$R_2$ represents a substituted or unsubstituted $C_{1-40}$ hydrocarbyl group;
$R_3$ and $R_5$ each independently represents a single bond, or a substituted or unsubstituted $C_{1-3}$ divalent alkyl group; and
$R_4$ represents a substituted or unsubstituted $C_{3-12}$ divalent alicyclic group,
wherein the term "substituted" means substituted with at least one $C_{1-4}$ linear or branched hydrocarbyl group, and
wherein the dicarboxylic acid monoester compound is selected from the group of maleic acid monoester, citraconic acid monoester, glutaconic acid monoester, 1,2-cyclopentanedicarboxylic acid monoester, 1,2-cyclohexanedicarboxylic acid monoester, tetrahydrophthalic acid monoester, and combinations thereof.

2. The fuel composition according to claim 1, wherein $R_1$ represents the unsubstituted $C_{2-4}$ divalent alkenyl group or the group having a structure of —$R_3$—$R_4$—$R_5$—;
$R_2$ represents a substituted or unsubstituted $C_{1-18}$ hydrocarbyl group;
$R_3$ and $R_5$ each independently represents a single bond or methylene; and
$R_4$ represents a substituted or unsubstituted $C_{3-10}$ divalent alicyclic group.

3. The fuel composition according to claim 1, wherein $R_2$ is selected from the group consisting of $C_{1-18}$ linear or branched hydrocarbyl groups, $C_{4-18}$ alicyclic hydrocarbyl groups, $C_{7-18}$ aryl-substituted hydrocarbyl groups, and $C_{7-18}$ hydrocarbyl-substituted aryl groups.

4. The fuel composition according to claim 1, wherein the dicarboxylic acid monoester compound has a concentration of 5 to 400 ppm, relative to a total mass of the fuel.

5. The fuel composition according to claim 1, wherein the dicarboxylic acid monoester compound is selected from the group consisting of monomethyl maleate, monoethyl maleate, mono-n-propyl maleate, mono-n-butyl maleate, mono-n-octyl maleate, mono-n-nonyl maleate, mono-n-decyl maleate, mono-n-dodecyl maleate, monoisopropyl maleate, monoisobutyl maleate, mono-sec-butyl maleate, mono-tert-butyl maleate, monoisooctyl maleate (mono-2-ethylhexyl maleate), monoisononyl maleate, monoisodecyl maleate, monoisoundecyl maleate, monoisotridecyl maleate, mono-p-nonylphenyl maleate, monobenzyl maleate, and combinations thereof.

6. The fuel composition according to claim 1, wherein the dicarboxylic acid monoester compound is selected from the group consisting of 1,2-cyclohexanedicarboxylic acid monoester, tetrahydrophthalic acid monoester, and combinations thereof.

7. A method for improving the lubricity of a fuel, comprising the step of adding a lubricity modifier to the fuel, wherein the lubricity modifier comprises a dicarboxylic acid monoester compound of formula (I):

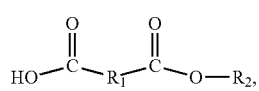

wherein $R_1$ represents a unsubstituted $C_{2-6}$ divalent alkenyl group or a group of formula —$R_3$—$R_4$—$R_5$—;
$R_2$ represents a substituted or unsubstituted $C_{1-40}$ aliphatic hydrocarbyl group;
$R_3$ and $R_5$ each independently represents a single bond, or a substituted or unsubstituted $C_{1-3}$ divalent alkyl group;
$R_4$ represents a substituted or unsubstituted $C_{3-12}$ divalent alicyclic group,
wherein the term "substituted" means substituted with at least one $C_{1-4}$ linear or branched hydrocarbyl group, and wherein the dicarboxylic acid monoester compound is selected from the group of maleic acid monoester, citraconic acid monoester, glutaconic acid monoester, 1,2-cyclopentanedicarboxylic acid monoester, 1,2-cyclohexanedicarboxylic acid monoester, tetrahydrophthalic acid monoester, and combinations thereof.

8. The method according to claim 7, wherein, in dicarboxylic acid monoester compound of formula (I),
$R_1$ represents the unsubstituted $C_{2-4}$ divalent alkenyl group or the group of formula —$R_3$—$R_4$—$R_5$—;
$R_2$ represents a substituted or unsubstituted $C_{1-18}$ saturated aliphatic hydrocarbyl group, alicyclic hydrocarbyl group or aryl group;
$R_3$ and $R_5$ each independently represents a single bond or methylene; and
$R_4$ represents a substituted or unsubstituted $C_{3-10}$ divalent alicyclic group.

9. The method according to claim 7, wherein, in dicarboxylic acid monoester compound of formula (I), $R_2$ is selected from the group consisting of $C_{1-18}$ linear or branched saturated aliphatic hydrocarbyl groups, $C_{4-18}$ alicyclic hydrocarbyl groups, $C_{7-18}$ aryl-substituted hydrocarbyl groups, and $C_{7-18}$ hydrocarbyl-substituted aryl groups.

10. The method according to claim 7, wherein the dicarboxylic acid monoester compound is selected from the group consisting of monomethyl maleate, monoethyl maleate, mono-n-propyl maleate, mono-n-butyl maleate, mono-n-octyl maleate, mono-n-nonyl maleate, mono-n-decyl maleate, mono-n-dodecyl maleate, monoisopropyl maleate, monoisobutyl maleate, mono-sec-butyl maleate, mono-tert-butyl maleate, monoisooctyl maleate (mono-2-ethylhexyl maleate), monoisononyl maleate, monoisodecyl maleate, monoisoundecyl maleate, monoisotridecyl maleate, monocyclohexyl maleate, mono-p-nonylphenyl maleate, monobenzyl maleate, and combinations thereof.

11. The method according to claim 7, wherein the dicarboxylic acid monoester compound is selected from the group consisting of 1,2-cyclohexanedicarboxylic acid monoester, tetrahydrophthalic acid monoester, and combinations thereof.

12. The method according to claim 7, wherein the concentration of the dicarboxylic acid monoester compound is 5 to 400 ppm, relative to a total mass of the fuel.

13. A dicarboxylic acid monoester compound of formula (I)

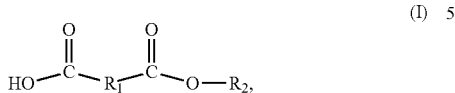
(I)

wherein $R_1$ represents a unsubstituted $C_{2-6}$ divalent alkenyl group or a group of formula —$R_3$—$R_4$—$R_5$—;
$R_2$ represents a substituted or unsubstituted $C_{5-14}$ linear or branched alkyl group;
$R_3$ and $R_5$ each independently represents a single bond, or a substituted or unsubstituted $C_{1-3}$ divalent alkyl group; and
$R_4$ represents a substituted or unsubstituted $C_{3-6}$ divalent alicyclic group,
wherein the term "substituted" means substituted with at least one $C_{1-4}$ linear or branched hydrocarbyl group.

14. The dicarboxylic acid monoester compound according to claim 13, selected from the group consisting of monoisononyl maleate (mono-7-methyl-1-octyl maleate), monoisoundecyl maleate, monoisotridecyl maleate, monoisononyl cyclohexanedicarboxylate, monoisononyl hexahydrophthalate, and monoisononyl methylhexahydrophthalate.

* * * * *